US010774381B2

(12) United States Patent
Cho et al.

(10) Patent No.: US 10,774,381 B2
(45) Date of Patent: Sep. 15, 2020

(54) GENETIC MARKER FOR DETERMINING MEAT QUALITY TRAITS OF PIGS AND USE THEREOF

(71) Applicants: Republic of Korea (Management : Rural Development Administration), Jeollabuk-do (KR); Korea Research Institute of Bioscience and Biotechnology, Daejeon (KR); Jeju National University Industry-Academic Corporation Foundation, Jeju-do (KR)

(72) Inventors: In Cheol Cho, Jeju-do (KR); Hee Bok Park, Jeju-do (KR); Jeong Woong Lee, Daejeon (KR); Jin Seop Ahn, Sejong-si (KR); Sang Hyun Han, Jeju-do (KR)

(73) Assignees: REPUBLIC OF KOREA (MANAGEMENT: RURAL DEVELOPMENT ADMINISTRATION), Jeollabuk-Do (KR); KOREA RESEARCH INSTITUTE OF BIOSCIENCES AND BIOTECHNOLOGY, Daejeon (KR); JEJU NATIONAL UNIVERSITY INDUSTRY-ACADEMIC COOPERATION FOUNDATION, Jeju-Do (KR)

( * ) Notice: Subject to any disclaimer, the term of this patent is extended or adjusted under 35 U.S.C. 154(b) by 70 days.

(21) Appl. No.: 15/804,009

(22) Filed: Nov. 6, 2017

(65) Prior Publication Data

US 2018/0135123 A1 May 17, 2018

(30) Foreign Application Priority Data

Nov. 15, 2016 (KR) ........................ 10-2016-0152247

(51) Int. Cl.
*C12Q 1/68* (2018.01)
*C07H 21/04* (2006.01)
(Continued)

(52) U.S. Cl.
CPC ............ *C12Q 1/6876* (2013.01); *A01K 67/02* (2013.01); *C12Q 1/6827* (2013.01);
(Continued)

(58) Field of Classification Search
None
See application file for complete search history.

(56) References Cited

U.S. PATENT DOCUMENTS

2018/0135123 A1   5/2018   Cho et al.

FOREIGN PATENT DOCUMENTS

EP         3 321 379        5/2018
KR    10-2004-0039059       5/2004
(Continued)

OTHER PUBLICATIONS

Cho et al. PLOS Genetics, vol. 15, No. 10, e1008279, Oct. 11, 2019 (Year: 2019).*

(Continued)

*Primary Examiner* — Jeanine A Goldberg
(74) *Attorney, Agent, or Firm* — Wenderoth, Lind & Ponack, L.L.P.

(57) ABSTRACT

The present invention relates to a genetic marker for determining meat quality traits of pigs and a use thereof, and specifically, a genetic marker for determining meat quality traits of pigs, comprising a polynucleotide consisting of 5 to 300 consecutive nucleotides comprising the nucleotides from the $1524^{th}$ to the $1527^{th}$ positions in the polynucleotide of SEQ ID NO: 1, or a polynucleotide complementary thereto, a composition for determining meat quality traits of pigs comprising an agent capable of detecting the genetic
(Continued)

marker, a composition for determining Korean native pigs, a kit, a microarray, a method for determining meat quality traits of pigs, and a method for determining meat quality traits of Korean native pigs. The genetic marker of the present invention is a specific marker for determining the meat quality traits of pigs, and thus the marker can be used not only as a means for the objective evaluation of meat quality traits of pigs that cannot be determined by the naked eye but also as a means for distinguishing between foreign pigs and Korean native pigs, and is thereby capable of contributing to the establishment of distribution order of pork meat.

1 Claim, 7 Drawing Sheets

Specification includes a Sequence Listing.

(51) Int. Cl.
  *C12Q 1/6876*    (2018.01)
  *C12Q 1/6888*    (2018.01)
  *A01K 67/02*    (2006.01)
  *C12Q 1/6827*    (2018.01)
  *G16B 20/00*    (2019.01)

(52) U.S. Cl.
  CPC ...... *C12Q 1/6888* (2013.01); *A01K 2227/108* (2013.01); *C12Q 2600/156* (2013.01); *C12Q 2600/166* (2013.01); *G16B 20/00* (2019.02)

(56) References Cited

FOREIGN PATENT DOCUMENTS

| KR | 10-2007-0113336 | 11/2007 |
|---|---|---|
| KR | 10-2014-0087786 | 7/2014 |
| KR | 10-2014-0092498 | 7/2014 |

OTHER PUBLICATIONS

Sus scrofa myosin-3 (LOC396711) mRNA at XM_013981330 (Sep. 11, 2015). (Year: 2015).*
Office Action dated Nov. 14, 2018 in corresponding Canadian Patent Application No. 2,984,938.
Luo et al., "Genome-Wide Association Analysis of Meat Quality Traits in a Porcine Large White × Minzhu Intercross Population", International Journal of Biological Sciences, vol. 8, No. 4, pp. 580-595, 2012.
Liu et al., "Genome-wide association analyses for meat quality traits in Chinese Erhualian pigs and a Western Duroc × (Landrace × Yorkshire) commercial population", Genetics Selection Evolution, vol. 47, No. 44, 11 pages, 2015.
Development of a New Line of Jeju Black Pig Improved for Both Lean Meat Production and Meat Quality Using Muscle Fiver Diagnosis System, 11_1543000_001240_01, Jan. 20, 2016.
Communication pursuant to Article 94(3) EPC dated Feb. 8, 2019 in European Patent Application No. 17200547.2.
Cho et al., "Association of a single nucleotide polymorphism in the 5' upstream region of the porcine myosin heavy chain 4 gene with meat quality traits in pigs", Animal Science Journal, vol. 87, No. 3, pp. 330-335, 2016.
Cho et al., "Genome-wide QTL analysis of meat quality-related traits in a large F2 intercross between Landrace and Korean native pigs", Genetics Selection Evolution, vol. 47, No. 7, 8 pages, 2015.
Li et al., "Analyses of porcine public SNPs in coding-gene regions by re-sequencing and phenotypic association studies", Molecular Biology Reports, vol. 38, No. 6, pp. 3805-3820, 2011.
Xiong et al., "Genome-wide association analysis reveals genetic loci and candidate genes for meat quality traits in Chinese Laiwu pigs", Mammalian Genome, vol. 26, No. 3-4, pp. 181-190, 2015.

* cited by examiner

Position on SSC12 (in Mb)

GENETIC MARKER FOR DETERMINING MEAT QUALITY TRAITS OF PIGS AND USE THEREOF

TECHNICAL FIELD

The present invention relates to a genetic marker for determining meat quality traits of pigs and use thereof, and specifically, a genetic marker for determining meat quality traits of pigs, containing a polynucleotide consisting of 5 to 300 consecutive nucleotides containing the nucleotides from the $1524^{th}$ to the $1527^{th}$ positions in the polynucleotide of SEQ ID NO: 1, or a complementary polynucleotide thereto, a composition for determining meat quality traits of pigs containing an agent capable of detecting the genetic marker, a composition for determining Korean native pigs, a kit, a microarray, a method for determining meat quality traits of pigs, and a method for determining meat quality traits of Korean native pigs.

BACKGROUND ART

There are about 200 breeds of pigs worldwide. Among them, European breeds account for about 33% and Asian breeds account for about 30%. These pig breeds can be easily distinguished based on phenotypic differences such as hair color, size, body shape, etc. However, in the case of lean meat, color, water-holding capacity, shearing force, etc., they vary with time and thus it is difficult even for specialists as well as ordinary people to distinguish pig breeds by the naked eye based on the meat of pigs. Recently, many efforts have been made to improve the quality of pig meat. Pigs are now being bred in Korea under certain standards or management using a scientific system, and Korean native pigs obtained as such are branded, and various brands of pig meat are already commercially available.

As part of this study, active studies are being conducted in the direction of discovering and developing methods to identify the breeds of pork meat using various DNA analysis methods. For example, Korean Patent Application Publication No. 10-2004-0039059 discloses a genetic detection method for selecting pigs with excellent phenotypic traits using specific DNA markers related to average daily gain, backfat thickness, and meat quality of pigs, and Korean Patent Application Publication No. 10-2007-0113336 discloses a DNA marker for detecting the increase in the number of pig muscle cells using single nucleotide polymorphism (SNP) by the difference in a single nucleotide sequence in the 5' promoter region of myogenin gene, which is known to be involved in myogenesis of pigs. However, the method for accurately determining the level of meat quality traits of pigs has not yet been developed, and additionally, the method for determining the level of meat quality of pigs using MYH3 gene has not been developed.

Under these circumstances, the present inventors have made efforts to develop a method for determining the quality of pork meat through genetic traits. As a result, they have confirmed that MYH3 gene is a gene capable of determining the meat quality of pigs and that it is possible to easily determine the meat quality of pigs determined genetically using the same, thereby completing the present invention.

DISCLOSURE

Technical Problem

An object of the present invention is to provide a genetic marker for determining meat quality traits of pigs, containing a polynucleotide consisting of 5 to 300 consecutive nucleotides containing the nucleotides from the $1524^{th}$ to the $1527^{th}$ positions in the polynucleotide of SEQ ID NO: 1, or a polynucleotide complementary thereto.

Another object of the present invention is to provide a composition for determining meat quality traits of pigs, containing an agent capable of detecting the genetic marker.

Still another object of the present invention is to provide a kit for determining meat quality traits of pigs containing the composition.

Still another object of the present invention is to provide a DNA microarray for determining meat quality traits of pigs containing the genetic marker.

Still another object of the present invention is to provide a method for determining meat quality traits of pigs, including: (a) amplifying the genetic marker from the DNA of a sample isolated from a subject; and (b) identifying the nucleotide sequence of the amplified product of step (a).

Still another object of the present invention is to provide a composition for determining Korean native pigs, containing an agent capable of detecting the genetic marker.

Still another object of the present invention is to provide a method for determining meat quality traits of Korean native pigs, including: (a) amplifying the genetic marker from the DNA of a sample isolated from a subject; and (b) determining the nucleotide sequence of the amplified product of step (a).

Technical Solution

To achieve the above objects, an aspect of the present invention provides a genetic marker for determining meat quality traits of pigs, containing a polynucleotide consisting of 5 to 300 consecutive nucleotides containing the nucleotides from the $1524^{th}$ to the $1527^{th}$ positions in the polynucleotide of SEQ ID NO: 1, or a polynucleotide complementary thereto.

In the present invention, it was confirmed that the meat quality traits of pigs (i.e., the intramuscular fat content and degree of redness) can be determined by MYH3 gene, and that there is a genetic variation in MYH3 gene between Korean native pigs and foreign pigs, and thus, the detection of a marker for MYH3 gene including the genetic variation will not only be able to determine the quality traits of pork meat, but also will be able to distinguish between the foreign pigs and Korean native pigs, thereby completing the present invention.

As used herein, the term "genetic marker" refers to a short DNA sequence used to identify genetic diversity caused by mutations or modifications in genetic loci.

For the purpose of the present invention, the genetic marker may refer to a gene in which a nucleotide variation occurs between pig species.

As used herein, the term "polynucleotide of SEQ ID NO: 1" refers to MYH3 gene. The term "MYH3 gene" refers to a gene encoding myosin heavy chain 3, one of the heavy chain proteins contained in the myosin that constitutes the muscle of an animal and the nucleotide sequence thereof can be obtained from a known database such as NCBI's GenBank (GenBank Accession No. KX549312), etc. In a specific embodiment, the gene may be a gene derived from pigs, but is not limited thereto.

The genetic marker of the present invention may be consecutive nucleotides of ACGT including the nucleotides from the $1524^{th}$ to the $1527^{th}$ positions in the polynucleotide of SEQ ID NO: 1, but is not limited thereto.

Additionally, the genetic marker may also include a polynucleotide which consists of 5 to 300 consecutive nucleotides, specifically 5 to 280 consecutive nucleotides, and more specifically 5 to 260 consecutive nucleotides, including the above nucleotides or a polynucleotide complementary thereto, but is not limited thereto.

As used herein, the term "meat quality traits" refers to a breed of phenotypic traits that represent the status of slaughtered pigs, excluding bones thereof, but may be intramuscular fat content, meat color, water-holding capacity, shearing force, etc., and more specifically, intramuscular fat content or meat color, but the phenotypic traits are not particularly limited thereto. Intramuscular fat content means the amount of fat contained in muscles and meat color means the color of meat identified by the naked eye, water-holding capacity is the ability of the livestock meat to maintain moisture, and shearing force means the toughness when tearing meat. In general, the meat quality is determined to be excellent as intramuscular fat content becomes high, meat color becomes red, and water-holding capacity or shearing force becomes low.

In the present invention, if the marker is detected in the pork, it may be determined that the intramuscular fat content of the given pork meat is high and the redness of meat color is increased compared to when the marker is not detected.

In a specific embodiment of the present invention, QTL analysis and linkage and linkage disequilibrium (LALD) mapping with regard to pig meat quality traits were performed on the offspring of pigs obtained by hybridization between Jeju native pigs with Landrace or Duroc pigs, and as a result, it was confirmed that the gene associated with the meat quality traits of pigs is MYH3 gene present in the 12$^{th}$ chromosome (FIGS. 2 to 4).

Additionally, as a result of the genotype analysis of MYH3 gene, it was confirmed that there is a genetic variation in the nucleotide sequence of MYH3 gene (QTN: i.e., MYH3-1805-1810delGGACTG) between Landrace (foreign pigs) and native pigs and foreign pigs (FIG. 11). Additionally, as a result of the cleavage of the causative nucleotide genetic variation by HpyCH4IV, a restriction enzyme, it was confirmed that the two different pig species have different gene cleavage patterns (FIG. 12).

This suggests that the genetic marker of the present invention can not only distinguish between foreign pigs and native pigs but also determine meat quality traits of pigs according to the distinction of species. Accordingly, it is expected that the level of meat quality traits can be accurately determined using the genetic marker of the present invention, and the genetic marker was first identified by the present inventors.

Another aspect of the present invention provides a composition for determining meat quality traits of pigs, which contains an agent capable of detecting the genetic marker.

As used herein, the term "agent capable of detecting a genetic marker" refers to an agent that can bind to the genetic marker of the present invention and thereby recognize or amplify the genetic marker, and in a specific embodiment, may refer to a primer or probe that can specifically bind to the genetic marker.

As used herein, the term "probe" refers to a nucleic acid fragment, which can specifically bind to mRNA, labeled with RNA, DNA, etc., corresponding to a few nucleotides at the shortest to a few hundred nucleotides at the longest. The probe may be prepared in the form of an oligonucleotide probe, a single-stranded DNA probe, a double-stranded DNA probe, an RNA probe, etc.

In the present invention, the probe that binds to and recognizes a genetic marker includes a sequence complementary to the polynucleotide sequence including the genetic marker, and may be in the form of DNA, RNA, or a DNA-RNA hybrid, but the probe is not limited thereto. Additionally, the probe may be additionally labeled with a fluorescent marker, a radiolabel, etc., to the 5' end or 3' end of the probe so that the probe can be recognized by the naked eye.

As used herein, the term "primer" refers to a short nucleotide sequence with a free 3' hydroxyl group, which can form a base pair with a complementary template and serve as a starting point for the replication of the template strand.

In the present invention, the primer used for the amplification of a genetic marker may be a single-stranded oligonucleotide that can act as a starting point for template-directed DNA synthesis under appropriate conditions of an appropriate buffer (e.g., 4 different nucleoside triphosphates and polymerases such as DNA polymerase, RNA polymerase, reverse transcriptase, etc.) and appropriate temperature for DNA synthesis, and the appropriate length of the primer may vary depending on the purpose of use. The primer sequence need not be completely complementary to a polynucleotide including the genetic marker or a complementary polynucleotide thereof, and may suffice if it is sufficiently complementary to hybridize.

Additionally, in a specific embodiment, the primer may be modified, for example, by methylation, capping, substitution of nucleotides, or modifications between nucleotides, such as uncharged linkers (e.g., methylphosphonate, phosphotriester, phosphoramidate, carbamate, etc.), or charged linkers (e.g., phosphorothioates, phosphorodithioates, etc.).

In the present invention, the primer may be a polynucleotide consisting of nucleotide sequences of SEQ ID NOS: 65 and 66, but is not limited thereto.

In a specific embodiment of the present invention, the nucleotide region having the nucleotide variation present between foreign pigs and native pigs was amplified using the primers of SEQ ID NOS: 65 and 66, and the "ACGT" region in the nucleotide sequence having the nucleotide variation was cleaved by HpyCH4IV, a restriction enzyme, and the resulting cleavage pattern was examined. As a result, it was confirmed that the difference in cleavage pattern between Landrace (a foreign pig species with poor meat quality) and Jeju native pigs (a Korean native pig species with good meat quality) by the restriction enzyme can be clearly distinguished (FIG. 12).

This suggests that the composition for determining the meat quality traits of pigs of the present invention can be effectively used not only for distinguishing between foreign pigs and native pigs but also for determining meat quality traits according to the distinction of pig species.

Another aspect of the present invention provides a kit for determining meat quality traits of pigs containing the composition.

The kit of the present invention can determine the level of meat quality traits of pigs by confirming the genetic marker of the present invention via amplification or by checking the mRNA expression levels of the genetic marker of the present invention. In a specific embodiment, the kit may be an RT-PCR kit or DNA chip kit, but is not limited thereto.

In a more specific embodiment, the kit may be a kit including essential factors necessary for performing RT-PCR. For example, the RT-PCR kit may include a test tube or other appropriate containers, a reaction buffer (with various pH values and magnesium concentrations), deoxynucleotides (dNTPs), dedeoxynucleotides (ddNTPs), enzymes such as Taq-polymerase and reverse transcriptase, DNAse, RNAse inhibitors, DEPC-water, sterile water, etc., in addition to each primer specific to the genetic marker. Additionally, the kit may also include a primer pair specific to the gene used as a quantitative control.

In still another specific embodiment, the kit of the present invention may be a DNA chip kit including essential elements necessary for performing a DNA chip assay.

As used herein, the term "DNA chip" refers to one of the DNA microarrays that can confirm each nucleotide of a few hundred thousand DNAs. Generally, the DNA chip kit is that where a gridded array of nucleic acid species is attached to a flat solid support plate (typically a glass surface no larger than a microscope slide), and is a device that enables multiple parallel hybridization reactions between the nucleic acid on a DNA chip and the complementary nucleic acid contained in a treated solution on a surface of the DNA chip, by constantly arraying nucleic acids on the surface of the DNA chip.

Still another aspect of the present invention provides a microarray for determining meat quality traits of pigs, including the genetic marker.

The microarray may be one which includes a DNA polynucleotide or RNA polynucleotide. The microarray may be prepared in a conventional microarray except that the polynucleotide of the present invention is included.

Methods for preparing a microarray by immobilizing a probe polynucleotide on a substrate are well known in the art. The probe polynucleotide, which is a hybridizable polynucleotide, refers to an oligonucleotide capable of sequence-specific binding to a complementary strand of a nucleic acid. The probe of the present invention is an allele-specific probe, where a polymorphic site is present in a nucleic acid fragment derived from two members of the same species and hybridizes to a DNA fragment derived from one member but not to a DNA fragment derived from the other member. In this case, the hybridization conditions show a significant difference in hybridization intensity between alleles and must be sufficiently stringent to hybridize to only one of the alleles. By doing so, good hybridization differences between different allelic forms can be induced. The probe of the present invention can be used for determining the meat quality traits of pigs by detecting alleles, etc. The determination methods may include detection methods based on hybridization of nucleic acids such as southern blot analysis, etc., and may be provided in a form already bound to a substrate of DNA chip in a method using a DNA chip. The hybridization may be performed under stringent conditions (e.g., a salt concentration of 1 M or less and a temperature of 25° C. or higher).

The process of immobilizing a probe polynucleotide associated with the determination of meat quality traits of pigs of the present invention on a substrate can also be easily performed using such a conventional technique. Additionally, the hybridization of nucleic acids on a microarray and detection of hybridization results are well known in the art. With regard to the detection, hybridization results can be detected, for example, by labeling a nucleic acid sample with a labeling material capable of generating a detectable signal including a fluorescent material, such as Cy3 and Cy5, hybridizing on a microarray, and detecting the signal generated from the labeled material.

Still another aspect of the present invention provides a method for determining meat quality traits of pigs, including: (a) amplifying the genetic marker from the DNA of a sample isolated from a subject; and (b) identifying the nucleotide sequence of the amplified product of step (a).

In the present invention, the method may further include determining that the meat quality traits of pigs are excellent compared to those of foreign pigs when the amplified product of step (b) includes consecutive nucleotides of ACGT.

As used herein, the term "subject" refers to a pig where the level of meat quality traits is to be confirmed, and the meat quality traits of the pig can be determined by analyzing the genotype included in the genetic marker using a sample obtained from the pig. The sample may be one such as hair, urine, blood, various body fluids, isolated tissues, isolated cells or saliva, etc., but is not particularly limited as long as the gene can be detected from the sample.

As used herein, the term "foreign pig" refers to pig species imported from countries other than Korea, conceptually opposite to Korean native pigs. Generally, it is known that foreign pigs are more vulnerable to diseases and have poor meat quality characteristics with regard to intramuscular fat, juiciness, meat tenderness, etc., compared to those of Korean native pigs. In a specific embodiment, the foreign pig may refer to Berkshire species, Yorkshire species, Duroc Jersey species, Hampshire species, Landrace species, etc., and for the purpose of the present invention, the foreign pig may refer to all breeds of pigs which were hybridized with foreign pigs.

In the present invention, the amplification of the genetic marker of the present invention from DNA in step (a) can be achieved by any method known to those skilled in the art. In a specific embodiment, the amplification method to be used may include PCR, ligase chain reaction (LCR), transcription amplification, self-sustained sequence replication, nucleic acid based sequence amplification (NABSA), etc., but the amplification method is not limited thereto.

Additionally, the determination of the nucleotides of the genetic marker contained in the amplified product of step (b) may be performed by any method known to those skilled in the art. In a specific embodiment, the determination may be performed by sequencing, mini-sequencing, allele-specific PCR, dynamic allele-specific hybridization (DASH), PCR extension analysis (e.g., single base extension (SBE)), PCR-SSCP, PCR-RFLP analysis or TaqMan technique, SNPlex platform (Applied Biosystems), mass spectrometry (e.g., MassRAY system of Sequenom), Bio-Plex system (Bio-Rad), restriction enzyme digestion method, etc., but the method for determination is not limited thereto and any method that can detect the consecutive nucleotides of ACGT contained in the amplified product may be used.

In a specific embodiment of the present invention, the nucleotide region having the nucleotide variation present between foreign pigs and native pigs was amplified using the primers of SEQ ID NOS: 65 and 66, and the "ACGT" region in the nucleotide sequence was cleaved by HpyCH4IV, a restriction enzyme, and the resulting cleavage pattern was examined. As a result, it was confirmed that the difference in cleavage pattern between Landrace (a foreign pig species with poor meat quality) and Jeju native pigs (a Korean native pig species with good meat quality) by the restriction enzyme can be clearly distinguished (FIG. 12).

This suggests that the method for determining the meat quality traits of pigs of the present invention can be effectively used not only for distinguishing between foreign pigs and native pigs but also for determining meat quality traits according to the distinction of pig species.

Still another aspect of the present invention provides a composition for determining Korean native pigs containing an agent capable of detecting the genetic marker.

In particular, the definite with regard to the term "agent capable of detecting a genetic marker" is the same as described above.

As used herein, the term "Korean native pigs" refers to pig species traditionally raised in Korea, as opposed to foreign pigs. In general, Korean native pigs are more resistant to diseases than foreign pigs, and have excellent meat quality characteristics such as intramuscular fat, juiciness, tenderness, etc. The Korean native pigs may be Chookjin Chamdon, Gangwon-do Sanuri Korean native pigs, Jeju native black pigs, Jeju dung pigs, etc., and more specifically, Jeju native pigs, but are not limited thereto. In the present invention, the term Korean native pig may be interchangeably used with "native pig", "traditional pig", or "Korean traditional pig".

In the present invention, when the marker is detected from a given pig, the pig can be determined as a Korean native pig compared to pigs from which the marker is not detected.

Still another aspect of the present invention provides a method for determining meat quality traits of pigs, which includes: (a) amplifying the genetic marker from the DNA of a sample isolated from a subject; and (b) identifying the nucleotide sequence of the amplified product of step (a).

In the present invention, when the consecutive nucleotides of ACGT are contained in the amplified product of step (b), the step (c) of determining the subject pig as a Korean native pig may be additionally included.

In particular, the definitions with regard to "subject" and "Korean native pig" are the same as described above.

In the present invention, the amplification of the genetic marker of the present invention from the DNA of step (a) may be performed by any method known to those skilled in the art. For example, the amplification may be performed by PCR, ligase chain reaction (LCR), transcription amplification, self-sustained sequence replication, nucleic acid based sequence amplification (NABSA), etc., but the amplification method is not limited thereto.

Additionally, the determination of the nucleotides of the genetic marker contained in the amplified product of step (b) may be performed by any method known to those skilled in the art. In a specific embodiment, the determination may be performed by sequencing, mini-sequencing, allele-specific PCR, dynamic allele-specific hybridization (DASH), PCR extension analysis (e.g., single base extension (SBE)), PCR-SSCP, PCR-RFLP analysis or TaqMan technique, SNPlex platform (Applied Biosystems), mass spectrometry (e.g., MassRAY system of Sequenom), Bio-Plex system (Bio-Rad), restriction enzyme digestion method, etc., but the method for determination is not limited thereto and any method that can detect the consecutive nucleotides of ACGT contained in the amplified product may be used.

In a specific embodiment of the present invention, the nucleotide region having the nucleotide variation present between foreign pigs and native pigs was amplified using the primers of SEQ ID NOS: 65 and 66, and the "ACGT" region in the nucleotide sequence was cleaved by HpyCH4IV, a restriction enzyme, and the resulting cleavage pattern was examined. As a result, it was confirmed that the difference in cleavage pattern between Landrace (a foreign pig species with poor meat quality) and Jeju native pigs (a Korean native pig species with good meat quality) by the restriction enzyme can be clearly distinguished (FIG. 12).

This suggests that the method for determining the meat quality traits of pigs of the present invention can be effectively used for distinguishing between foreign pigs and native pigs.

Advantageous Effects of the Invention

The genetic marker of the present invention, which is a specific marker for determining the meat quality traits of pigs, can be used not only for objective evaluation of meat quality traits of pigs which are not visually distinguishable but also as a means for discriminating foreign pigs from Korean native pigs. As a result, the genetic marker of the present invention will contribute to the establishment of distribution order of pork meat.

BRIEF DESCRIPTION OF DRAWINGS

In FIG. 7, (a) shows an image illustrating the transcriptional activity of MYH3 gene, in which P/C indicates a positive control, and the numbers in red (21, 24, 26, 27, and 28) indicate transgenic mice that exhibit transcription activity of MYH3 gene, the numbers in black (19, 20, 22, 23, and 25) indicate transgenic mice that do not exhibit transcription activity of MYH3 gene; and (b) shows an image illustrating the results of western blot analysis with regard to protein expression level of MYH3 gene.

FIG. 9(b) shows images illustrating a histochemical staining of hindlimb muscle tissue with myosin ATPase, in which red arrows indicate Type 1/oxidative/slow fibers, which is a kind of red muscle; blue arrows indicate Type 2a, which is a kind of white muscle; blue triangles indicate Type 2/glycolytic/fast fibers of Type 2b, which is a kind of white muscle; and the scale bar indicates 50 μm. FIG. 9(c) shows images of hindlimb muscle tissue stained with Oil red 0, in which the scale bar indicates 100 µm, and the areas present in the rectangles are enlarged and shown therebelow.

FIG. 10(a) shows the results of qRT-PCR and western blot analysis with regard to mRNA and protein expression of genes related to myofiber type, using four-month-old wild-type mice (n=3) and transgenic mice (n=5). FIG. 10(b) shows the results of qRT-PCR analysis of the mRNA expression levels of genes related to the slow-type (left) and fast-type (right) muscles of the hindlimb muscles, using four-month-old wild-type mice (n=3) and transgenic mice (n=4). The results were obtained in three independent experiments, which were expressed as mean±SEM (*P<0.05, **P<0.01). FIG. 10(c) shows the results of Hematoxylin and Eosin stained hindlimb muscles, in which the arrows indicate perimysium and the triangles indicate endomysium. FIG. 10(d) shows the results of qRT-PCR analysis with regard to mRNA expression levels of adipogenesis-related genes.

DETAILED DESCRIPTION OF THE INVENTION

Hereinafter, the present invention will be described in more detail with reference to the following Examples. However, these Examples are for illustrative purposes only and the invention is not intended to be limited by these Examples.

Example 1. Visual Comparison of Meat Quality Traits of Pigs

For comparison of meat quality traits (intramuscular fat content and red meat) between Jeju native black pigs and Landrace pigs, the shapes of sirloins of these pigs were analyzed.

Figure 1:
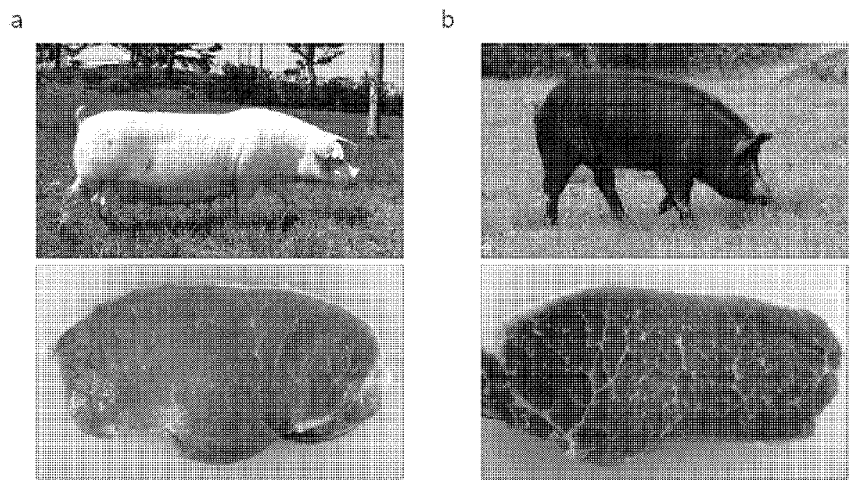
FIG. 1 shows images comparing the appearance and sirloin between Landrace (a) (an introduced species) and Korean native pigs (b) (a native species).

As a result, as shown in FIG. 1, it was confirmed that the sirloin meat of Landrace pigs, which is an introduced species, was white but pale while the sirloin meat of Jeju native pigs had a black coat color and red meat, and particularly had excellent marbling deposition.

From the above results, it was found that the meat quality of Jeju native pigs is superior to that of Landrace pigs.

Example 2. Quantitative Trait Locus (QTL) Analysis of Pig Meat Quality

Example 2-1. Confirmation of QTL of Meat Quality Gene

For confirmation of genes capable of determining the meat quality traits of pigs, quantitative trait locus (QTL) analysis was performed with regard to meat quality traits (degree of redness (a*) and intramuscular fat content (IMF)) using a progeny (LK herd) obtained by hybridization between a Jeju native pig with a Landrace pig and a progeny (DK herd) obtained by hybridization between a Jeju native pig and a Duroc pig.

Figure 2:
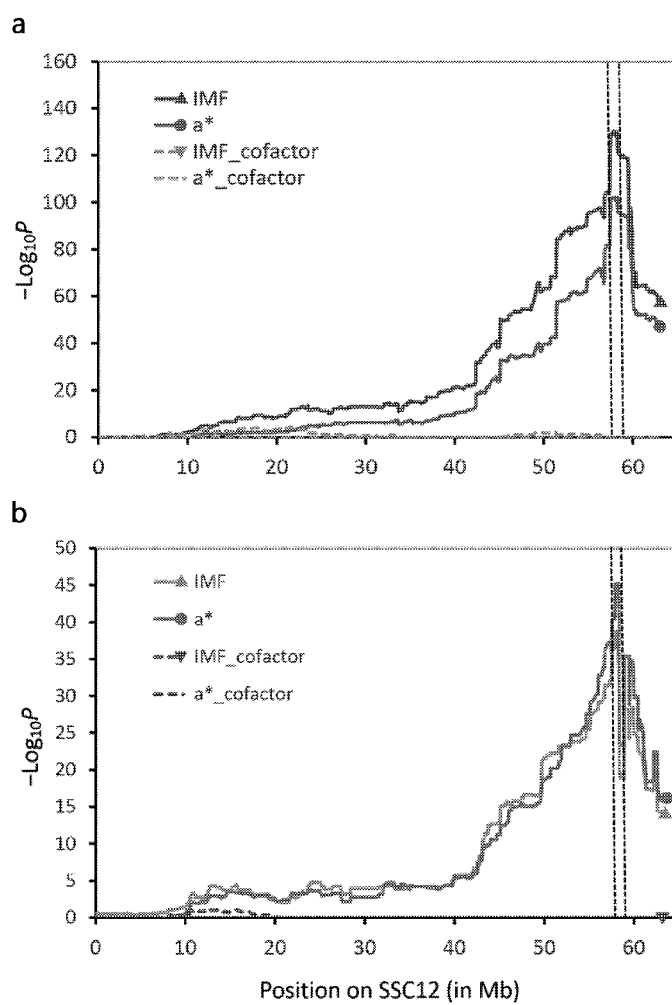
FIG. 2 shows graphs illustrating the results of linkage-linkage disequilibrium analysis (LLDA) according to the confirmation of quantitative trait locus (QTL) region of a gene for determining meat quality traits, in which (a) relates to a progeny (LK herd) obtained by hybridization between a Jeju native pig with a Landrace pig and (b) relates to a progeny (DK herd) obtained by hybridization between a Jeju native pig and a Duroc pig.

As a result, as shown in FIG. 2(a), it was confirmed that the vertical dotted line in the LK group is located on the 661 kb region of chromosome 12, and additionally, as shown in FIG. 2(b), it was confirmed that the vertical dotted line in the KD group is located on the 661 kb region of chromosome 12.

From the above results, it was confirmed that the genes capable of determining the red meat (degree of redness) and intramuscular fat content were present in the same position regardless of the pig species, and it was found that the genes exist in the 661 kb region of chromosome 12.

Example 2-2. Confirmation of Genes Related to Meat Quality Traits of Pigs

As it was confirmed that the genes capable of determining the meat quality traits of pigs exist in the 661 kb region of chromosome 12 in Example 2-1, the genes located in the region were confirmed by LALD mapping.

Figure 3:
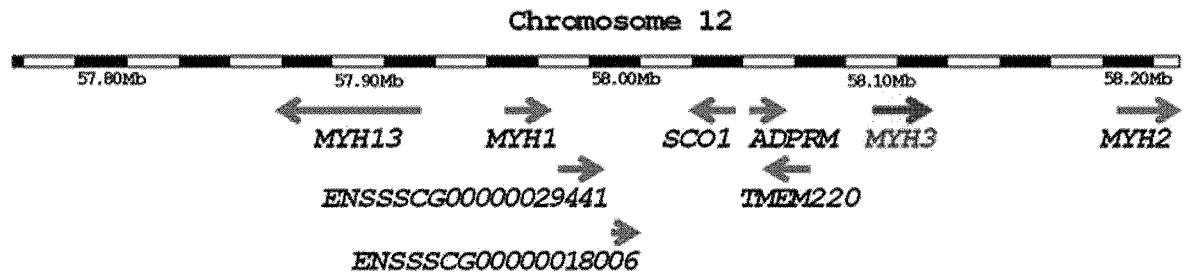
FIG. 3 shows the results of LALD mapping illustrating the genes present in the QTL region of the gene for determining meat quality traits.

As a result, as shown in FIG. 3, it was confirmed that a total of nine genes (MYH3, MYH1, MYH2, MYH13, ADPRM4, SCO1, TMEM4220, ENSSSCG00000029441, and ENSSSCG00000018006) exist in the region of genes related to meat quality traits.

Example 2-3. Selection of Genes Related to Meat Quality Traits of Pigs

As the nine genes capable of determining the meat quality traits of pigs were confirmed, an attempt was made to select the gene which is most closely related to the determination of meat quality traits.

The relative mRNA expression levels of the nine genes were analyzed in sirloin (longissimus) and hindlimb muscles (quadriceps) of Landrace pigs and Korean native pigs (KNP).

Specifically, sirloin and hindlimb muscles were collected from Landrace pigs and Korean native pigs (KNP) and RNA was isolated therefrom using Trizol reagent (Ambion). After adjusting the RNA concentration of each tissue to 5 µg, cDNA (complementary DNA) was synthesized using the TOPscript cDNA synthesis kit (Enzynomics). Then, qRT-PCR was performed using cDNA of each tissue. A total of 40 cycles of QRT-PCR were performed at 95° C. for 20 sec, at 60° C. for 20 sec, and at 72° C. for 20 sec. The QRT-PCR was performed using the QuatiTect SYBR Green PCR Kit (Qiagen), and analyzed in real time using the Rotor-Gene Q thermal cycler (Qiagen) instrument. The primers used for the analysis of the total of nine genes are listed in Table 1 below.

TABLE 1

| Gene | Category | Direction | Nucleotide Sequence (5'→3') |
|---|---|---|---|
| pMYH3 | SEQ ID NO: 3 | Forward | AAAAGCTCAGCATGAGCTCGA |
| | SEQ ID NO: 4 | Reverse | AGGGTCAGGAACCATGAAAAT |
| pMYH1 | SEQ ID NO: 5 | Forward | GTTCTGAAGAGGGTGGTAC |
| | SEQ ID NO: 6 | Reverse | AGATGCGGATGCCCTCCA |
| pMYH2 | SEQ ID NO: 7 | Forward | GGGCTCAAACTGGTGAAGC |
| | SEQ ID NO: 8 | Reverse | AGATGCGGATGCCCTCCA |
| pMYH13 | SEQ ID NO: 9 | Forward | CACAGGGCTCTGGCCGACAT |
| | SEQ ID NO: 10 | Reverse | CGTGCGCACAGGGGTGTAGT |
| pADPRM | SEQ ID NO: 11 | Forward | CATCCTGAGACCGTGCCTTCA |
| | SEQ ID NO: 12 | Reverse | TTCCGCATTTGGGTTGTGCT |
| pSCO1 | SEQ ID NO: 13 | Forward | TCCTCACGGACTCGGGGTTT |
| | SEQ ID NO: 14 | Reverse | GTGGGGTCTCTGCTGCCCTT |
| pTMEA1220 | SEQ ID NO: 15 | Forward | CCCAGACGCAGAACTGTGGG |
| | SEQ ID NO: 16 | Reverse | GTTGTATGCCAAGCCGGCAG |
| pENSSSCG 00000029441 | SEQ ID NO: 17 | Forward | TCGTGCTGGAGCAGGAGGAG |
| | SEQ ID NO: 18 | Reverse | AGGTGTCTGTGGCCTTGGGG |
| pENSSSCG 00000018006 | SEQ ID NO: 19 | Forward | AGAACCAGCCCTTCGATGCC |
| | SEQ ID NO: 20 | Reverse | TGGCATACACATCCTCCGGC |
| pGAPDH | SEQ ID NO: 21 | Forward | GGGCATGAACCATGAGAAGT |
| | SEQ ID NO: 22 | Reverse | GGGCATGAACCATGAGAAGT |

Figure 4:
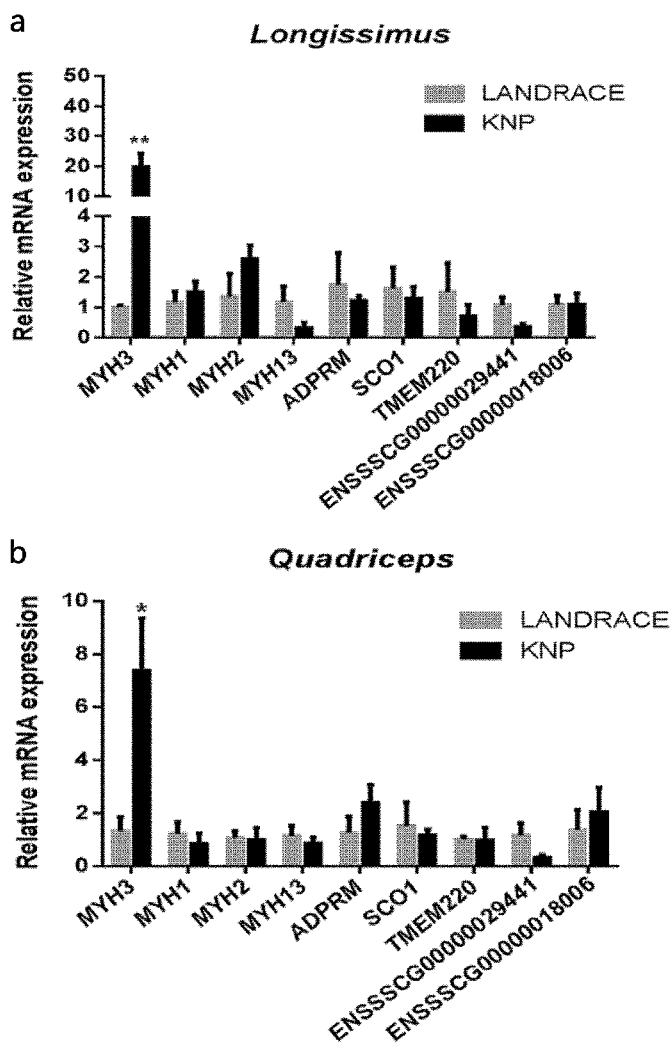
FIG. 4 shows graphs comparing mRNA expression levels of the genes present in the QTL region, in which (a) relates to sirloin (longissimus) and (b) relates to hindlimb muscles (quadriceps).

As a result, as shown in FIGS. 4(a) and 4(b), mRNA expression of the MYH3 gene was significantly higher in the sirloin and hindlimb muscles of Korean native pigs compared to those of Landrace pigs.

These results confirmed that the MYH3 gene is a major gene that determines the degree of redness and intramuscular fat content, among the meat quality traits of pigs.

Example 3. Preparation of Transgenic Mouse Inserted with Porcine MYH3 Gene

As it was confirmed in Example 2 that MYH3 gene is the gene that can determine meat quality traits of pigs (in particular, degree of redness and intramuscular fat content), transgenic mice inserted with porcine MYH3 gene were prepared according to the methods described in Examples 3-1 to 3-2 and the in vivo activity of MYH3 gene was confirmed using the transgenic mice.

Example 3-1. Preparation of Transgenic Vector

First, for the preparation of a transgenic mouse inserted with a porcine MYH3 gene, a recombinant CAGGS-MYH3-Flag expression vector inserted with a porcine MYH3 gene was prepared.

Specifically, for the preparation of a vector capable of overexpressing the porcine MYH3 gene, the entire nucleotide sequence of the mRNA of the porcine MYH3 gene was confirmed. Then, the confirmed sequence was divided into a total of 4 different fragments and each fragment of the sequence was synthesized artificially. The first fragment was 1,417 bp long and artificially synthesized by adding XbaI and BglII sites at both ends. The second fragment was 1,745 bp long and BglII and SalI sites were added at both ends; the third fragment was 1,777 bp long and SalI and SacII sites were added at both ends; and finally the fourth fragment was 944 bp long and SacII and EcoRI sites were added at both ends. The completed four DNA fragments were ligated through the restriction enzyme sites artificially added to the ends so as to finally complete a gene fragment containing the entire mRNA sequence of the porcine MYH3 gene.

Figure 5:
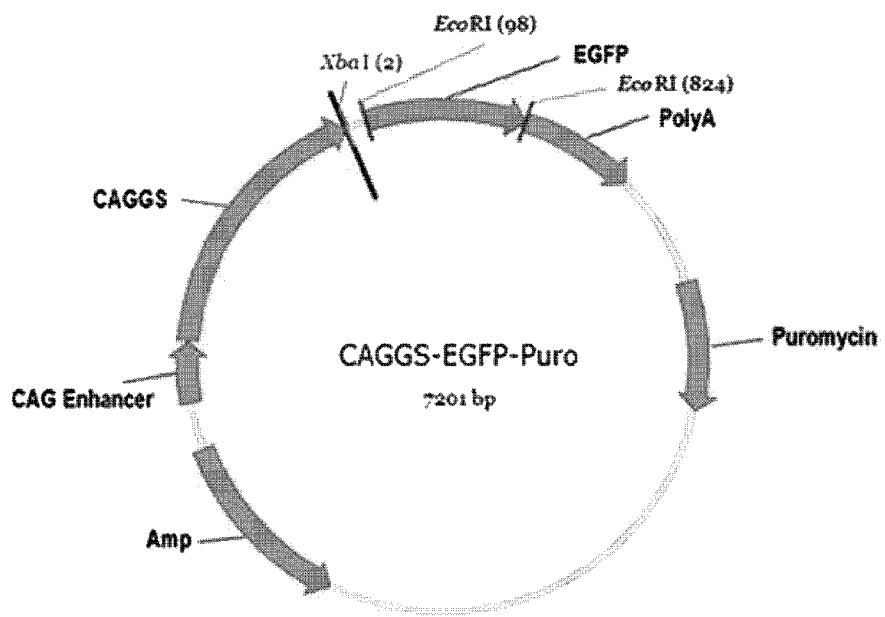
FIG. 5 shows a cleavage map of CAGGS-EGFP-Puro vector.
Figure 6:
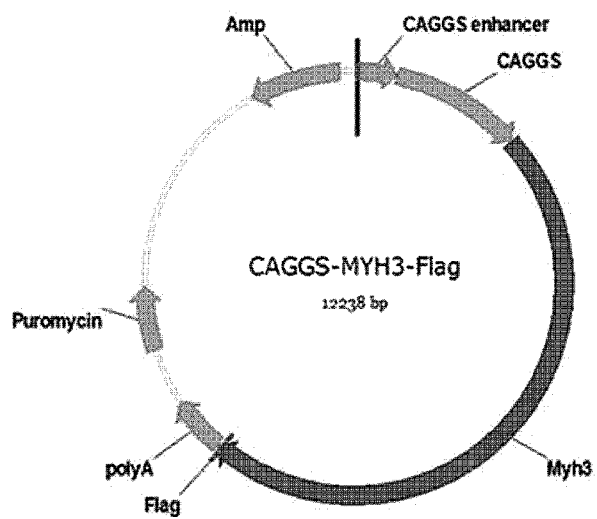
FIG. 6 shows a cleavage map of CAGGS-MYH3-Flag expression vector in which MYH3 gene was recombined and the sequence of the genes within the vector.
Figure 6:
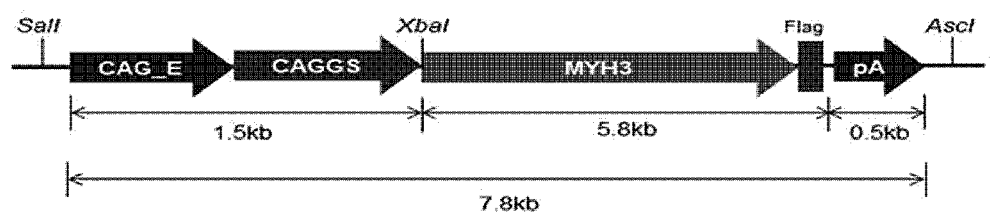

Then, the CAGGS-EGFP-Puro vector as shown in FIG. 5 was digested with XbaI and EcoRI, and then, the entire mRNA fragment of the porcine MYH3 gene prepared in advance was inserted into the digested CAGGS-EGFP-Puro vector to finally prepare a porcine MYH3-transgenic vector (FIG. 6).

The structure of the vector is shown in FIG. 6 and the nucleotide sequence of the vector is indicated by SEQ ID NO: 2.

Example 3-2. Preparation of Transgenic Mouse

Example 3-2-1. Method of Preparing Transgenic Mouse

A transgenic mouse was prepared using the vector prepared in Example 3-1.

Specifically, the fertilized eggs of C57BL/6n mice were obtained and the transformed vector prepared above was introduced into the nuclei of the embryos by microinjection.

As a result, a total of 47 F0 founders were confirmed.

Example 3-2-2. Confirmation of Introduction of Exogenous Gene (MYH3) by Analysis of mRNA Expression In order to confirm whether MYH3 gene was introduced into the transgenic mouse prepared in Example 3-2-1, the expression of the mRNA of the MYH3 gene was analyzed.

Specifically, the PCR was performed under the conditions of 30 sec at 95° C., 30 sec at 60° C., and 30 sec at 72° C., for a total of 40 cycles, and the primers used are listed in Table 2 below.

TABLE 2

| Gene | Category | Direction | Nucleotide Sequence (5'→3') |
|---|---|---|---|
| pMYH3 | SEQ ID NO: 23 | Forward | CCGAGAGCTGGAGTTTGA |
|  | SEQ ID NO: 24 | Reverse | CTCCCATATGTCCTTCCGAGT |

Figure 7:
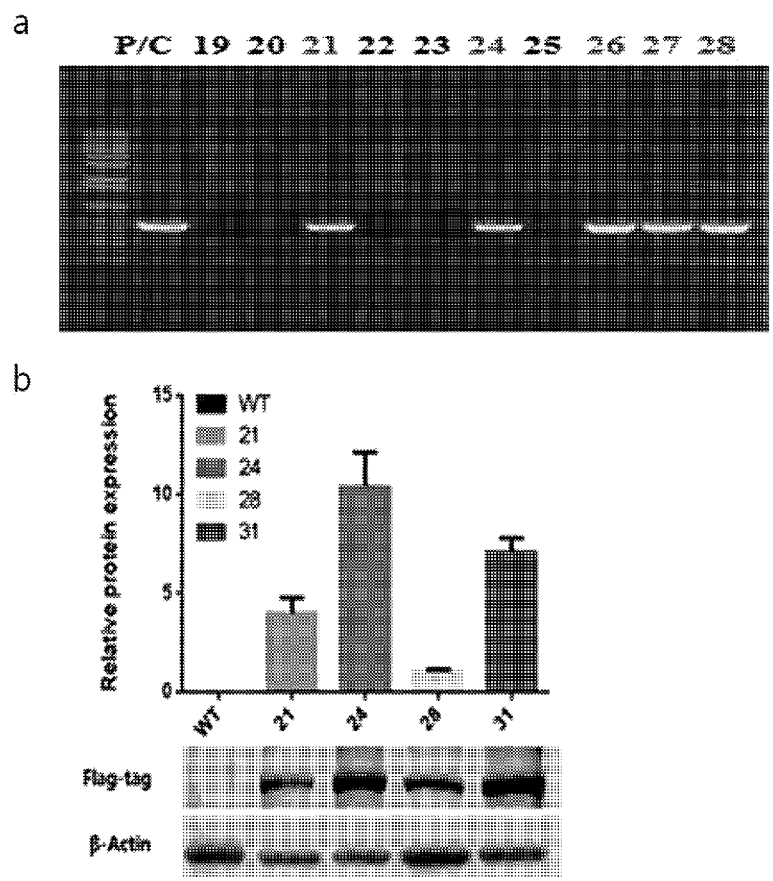
FIG. 7 shows the activity and expression pattern of MYH3 gene in a transgenic mouse transformed with a vector in which MYH3 gene was recombined.

As a result, as shown in FIG. 7(a), the transgenic mice (Nos. 21, 24, 26, 27, and 28) in which the MYH3 gene was inserted and expressed the mRNA of the MYH3 gene was confirmed.

Example 3-2-3. Confirmation of Introduction of Foreign Gene by Analysis of Protein Expression In order to confirm whether MYH3 gene was introduced into the transgenic mouse prepared in Example 3-2-1, the expression of the protein of the MYH3 gene was analyzed.

Specifically, the hindlimb muscle tissues of the wild-type mouse (WT) and the transgenic mouse (TG) were collected and the muscle tissues were broken down by ultrasonication in RIPA buffer after adding a protease inhibitor thereto. Then, proteins were isolated from the tissues using a low-temperature centrifuge and the proteins were recovered from the supernatant. The recovered proteins were quantified using a BSA protein assay reagent (Bio-rad) and heated at 100° C. for about 10 minutes with 4× protein loading buffer (1×). To perform a western blot using the prepared proteins, the proteins were electrophoresed on SDS-PAGE gel for about 2 hours. Then, the proteins were transferred to a PVDF membrane and blocked with 5% skim milk for 1 hour, and anti-Flag M2 (F1804, Sigma-Aldrich) and β-actin (#4970, Cell Signaling) were added thereto and reacted overnight at 4° C. On the next day, the resultant was washed with TBST solution, reacted with the secondary antibody for 2 hours, treated with ECL reagent, and signals of antibody bound to the proteins were detected using the LAS-300 luminescent image analyzer system (Fujifilm). The secondary antibody used in the experiment varied depending on the primary antibody.

Figure 8:
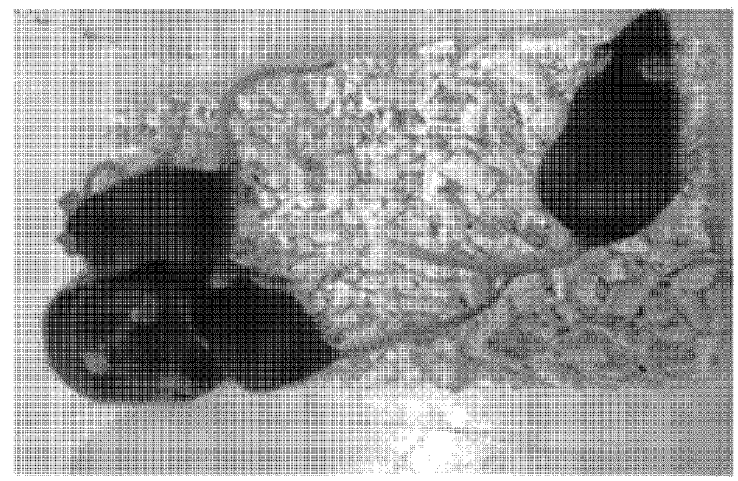
FIG. 8 shows an image of transgenic mice in which a porcine MYH3 gene is inserted.

As a result, as shown in FIG. 7(b), the highest level of the MYH3 gene expression was found in the transgenic mouse No. 24 among the transgenic mice. Accordingly, hybridization was performed using the transgenic mouse No. 24 having the highest expression level of the protein of the transgene and bread, and the image of the resulting mice is shown in FIG. 8.

Example 3-3. Confirmation of Muscle Morphology of Transgenic Mouse

In order to confirm the function of the MYH3 gene in determining meat quality traits, the meat quality traits of the transgenic mouse prepared in Example 3-2 were examined.

Figure 9:
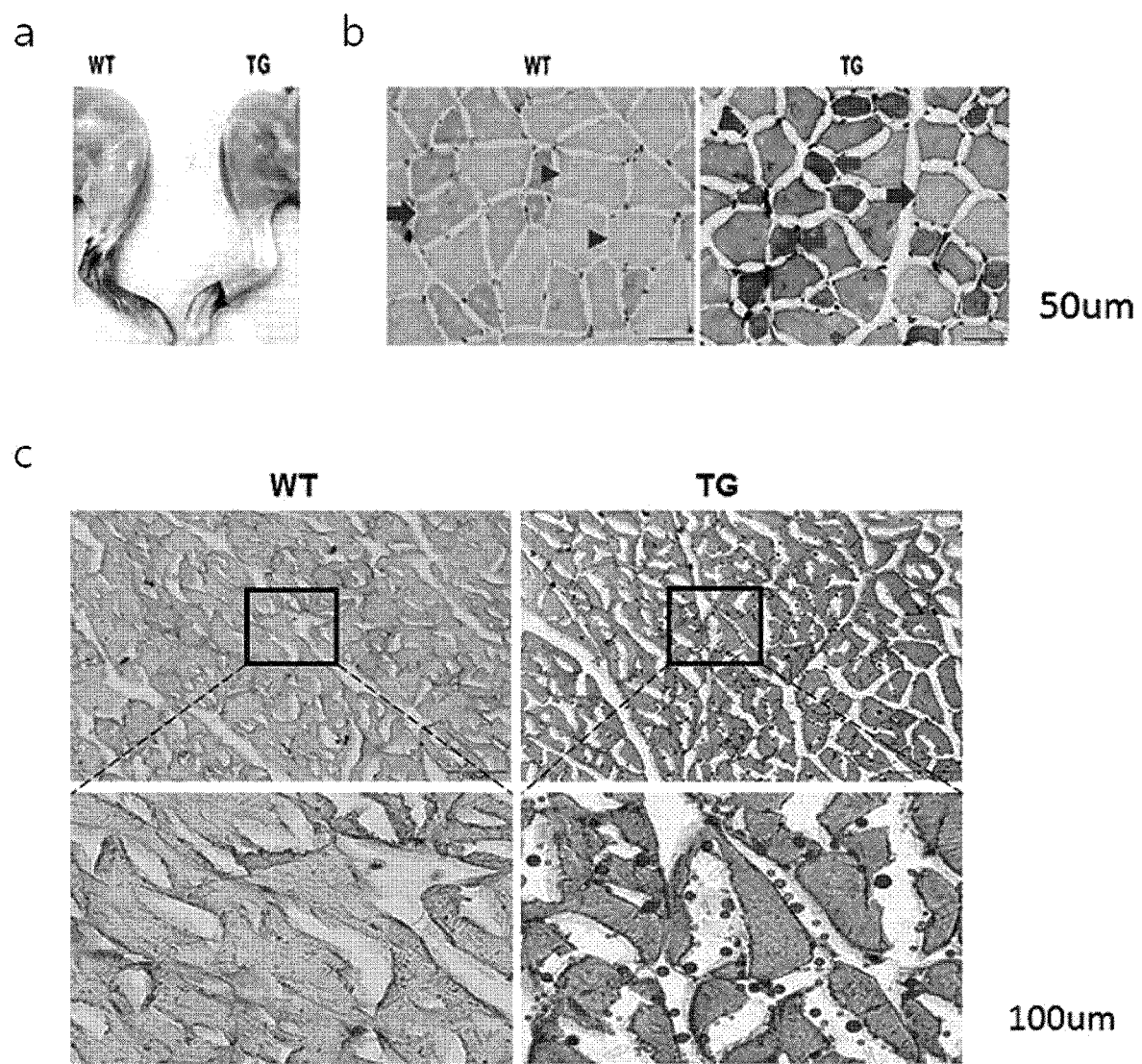
FIG. 9 shows images illustrating the appearance of the hindlimb muscle (a) and the hindlimb muscle tissue ((b) and (c)) of a wild-type mouse (WT) and a transgenic mouse (TG).

First, as shown in FIG. 9(a), the hindlimb muscle of the transgenic mouse (right; TG) was found to be redder compared to that of the wild-type mouse (left; WT).

Then, ATPase staining was performed so as to further confirm the muscle morphology. The hindlimb muscle samples of wild-type and transgenic mouse were collected and treated overnight in a 30% sucrose solution. The muscles were tissue-sectioned to 10 μm at −25° C. using OCT compounds and fixed with 4% PFA for 1 hour. The tissue sections were washed with running water for 10 minutes and washed again with 60% isopropanol, and subjected to an experiment using the ATPase stain lyophilized powder for histoenzymatic reaction kit (Bio Optica) according to the manufacturer's manual.

As a result, as shown in FIG. 9(b), it was confirmed that the transgenic mouse (right; TG), in which the MYH3 gene was inserted, had more red muscle distributed in the hind limb muscle than the wild-type mouse.

Additionally, Oil Red 0 staining was performed to determine fat distribution in muscle tissue. Specifically, the tissue sections were reacted with a 0.3% Oil Red 0 solution for 1 hour.

As a result, as shown in FIG. 9(c), it was found that the level of staining in the transgenic mouse (TG) was stronger compared to that of the wild-type mouse (left; WT) thus confirming that hindlimb muscle of the transgenic mouse has a higher fat content compared to that of the wild-type mouse.

In summary, it was confirmed that the MYH3 gene is the gene causing the accumulation of red muscle to improve redness of the meat and the accumulation of muscle fat content.

Example 3-4. Confirmation of Gene Expression Pattern within Muscle of Transgenic Mouse

Example 3-4-1. Confirmation of Expression Pattern of White Muscle/Red Muscle-Forming Gene In order to confirm the function of the MYH3 gene related to the determination of the meat quality traits, the expression pattern of the white muscle/red muscle-forming gene of the transgenic mouse prepared in Example 3-2 was examined.

Specifically, the hindlimb muscle tissue samples of the wild-type mouse (WT) and the transgenic mouse (TG) were collected and qRT-PCR was performed according to the method of Example 2-3. The primers used are listed in Table 3 below.

TABLE 3

| Gene | Category | Direction | Nucleotide Sequence (5'→3') |
|---|---|---|---|
| Myh7 | SEQ ID NO: 25 | Forward | AGTCCCAGGTCAACAAGCTG |
|  | SEQ ID NO: 26 | Reverse | TTCCACCTAAAGGGCTGTTG |
| Myh2 | SEQ ID NO: 27 | Forward | AGTCCCAGGTCAACAAGCTG |
|  | SEQ ID NO: 28 | Reverse | GCATGACCAAAGGTTTCACA |
| Myh1 | SEQ ID NO: 29 | Forward | AGTCCCAGGTCAACAAGCTG |
|  | SEQ ID NO: 30 | Reverse | CACATTTTGCTCATCTCTTTG |

TABLE 3-continued

| Gene | Category | Direction | Nucleotide Sequence (5'→3') |
|---|---|---|---|
| Myh4 | SEQ ID NO: 31 | Forward | AGTCCCAGGTCAACAAGCTG |
|  | SEQ ID NO: 32 | Reverse | TTTCTCCTGTCACCTCTCAACA |
| Myoglobin | SEQ ID NO: 33 | Forward | GCAAGGCCCTGGAGCTCTTC |
|  | SEQ ID NO: 34 | Reverse | GCTTGGTGGGCTGGACAGTG |
| Tnnt1 | SEQ ID NO: 35 | Forward | CCCCCGAAGATTCCAGAAGG |
|  | SEQ ID NO: 36 | Reverse | TGCGGTCTTTTAGTGCAATGAG |
| Tnni1 | SEQ ID NO: 37 | Forward | ATGCCGGAAGTTGAGAGGAAA |
|  | SEQ ID NO: 38 | Reverse | TCCGAGAGGTAACGCACCTT |
| Tnnc1 | SEQ ID NO: 39 | Forward | GCGGTAGAACAGTTGACAGAG |
|  | SEQ ID NO: 40 | Reverse | CCAGCTCCTTGGTGCTGAT |
| Aldoa | SEQ ID NO: 41 | Forward | ACTCTCTGCTGACCGGGCTCT |
|  | SEQ ID NO: 42 | Reverse | AATGCTTCCGGTGGACTCAT |
| Pvalb | SEQ ID NO: 43 | Forward | ATCAAGAAGGCGATAGGAGCC |
|  | SEQ ID NO: 44 | Reverse | GGCCAGAAGCGTCTTTGTT |
| Tnnt3 | SEQ ID NO: 45 | Forward | GGAACGCCAGAACAGATTGG |
|  | SEQ ID NO: 46 | Reverse | TGGAGGACAGAGCCTTTTCTT |
| Tnni2 | SEQ ID NO: 47 | Forward | AGAGTGTGATGCTCCAGATAGC |
|  | SEQ ID NO: 48 | Reverse | AGCAACGTCGATCTTCGCA |
| Tnnc2 | SEQ ID NO: 49 | Forward | ATGGCAGCGGTACTATCGACT |
|  | SEQ ID NO: 50 | Reverse | CCTTCGCATCCTCTTTCATCTG |
| GAPDH | SEQ ID NO: 51 | Forward | GAAGGGCATCTTGGGCTACAC |
|  | SEQ ID NO: 52 | Reverse | GCAGCGAACTTTATTGATGGTATT |

Additionally, western blot was performed according to method of Example 3-2-3, in which the primary antibodies used are as follows: Anti-Flag M2 (F1804, Sigma-Aldrich), MYH7 (SC-53089, Santa Cruz Biotechnology), MYH4 (H00004622-B01P, Abnova), and β-actin (#4970, Cell signaling).

Figure 10:
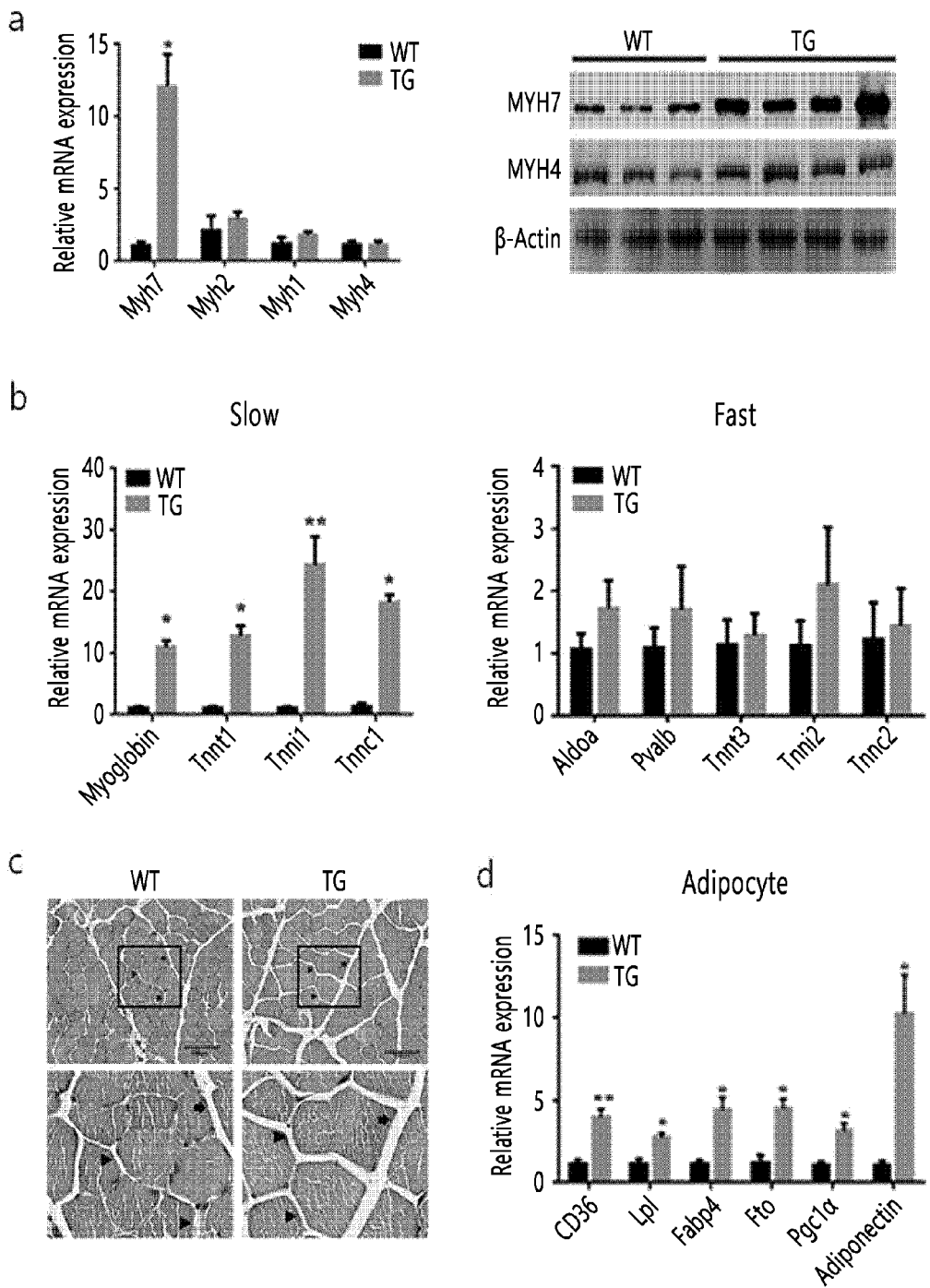
FIG. 10 shows results confirming the gene expression pattern in the muscle of transgenic mice in which porcine MYH3 gene is inserted.

As a result, as shown in FIG. 10(a), the mRNA and protein expression of the MYH7 gene, which is a slow-type gene related to a type of red muscle, were rapidly increased in the transgenic mouse compared to the wild-type mouse.

As shown in FIG. 10(b), there was no significant difference in the expression level of the fast-type genes related to a type of white muscle (Aldoa, Pvalb, Tnnf3, Tnnl2, and Tnnc2), in the transgenic mouse compared to that of the wild-type mouse; however, the mRNA expression levels of all of genes related to the type of red muscle (Myoglobin, Tnnt1, Tnnl1, and Tnnc1) were increased compared to that of the wild-type mouse.

Example 3-4-2. Confirmation of Fat Accumulation Pattern and Expression Pattern of Related Genes In order to confirm the function of the MYH3 gene in determining the meat quality traits, the fat accumulation pattern and the expression pattern of the related genes of the transgenic mouse prepared in Example 3-2 were examined.

First, for the confirmation of a fat accumulation pattern, an attempt was made to examine the morphology of tissues, and for this purpose, the tissues were subjected to Hematoxylin and Eosin (H & E) staining. The muscle tissues of the wild-type mouse (WT) and the transgenic mouse (TG) were subjected to paraffin embedding and then cut into a thickness of 4 μm. Then, paraffin was removed using xylene, dehydrated with 100%, 95%, 75%, and 50% alcohol in this order, and washed for 5 minutes in running water. Then, the tissues were treated with Mayer's hematoxylin solution for 1 minute, washed with running water for 20 minutes, treated with eosin for 1 minute, followed by dehydration and clearing, and then the stained state of the tissues was examined under a microscope.

In order to confirm the expression pattern of the fat accumulation gene in the muscle tissue of the transgenic mouse, qRT-PCR was performed according to method of Example 2-3. In particular, the primers used are listed in Table 4 below.

TABLE 4

| Gene | Category | Direction | Nucleotide Sequence (5'→3') |
|---|---|---|---|
| CD36 | SEQ ID NO: 53 | Forward | AATGGCACAGACGCAGCCT |
|  | SEQ ID NO: 54 | Reverse | GGTTGTCTGGATTCTGGA |
| LPL | SEQ ID NO: 55 | Forward | GTACCTGAAGACTCGCTCTC |
|  | SEQ ID NO: 56 | Reverse | AGGGTGAAGGGAATGTTCTC |
| Fabp4 | SEQ ID NO: 57 | Forward | GATGCCTTTGTGGGAACCTG |
|  | SEQ ID NO: 58 | Reverse | TCCTGTCGTCTGCGGTGATT |

TABLE 4-continued

| Gene | Category | | | Direction | Nucleotide Sequence (5'→3') |
|---|---|---|---|---|---|
| Fto | SEQ ID NO: | 59 | Forward | GTCAGAGAGAAGGCCAATGA |
| | SEQ ID NO: | 60 | Reverse | TAGCAGTCTCCCTGGTGAAG |
| Pgc1a | SEQ ID NO: | 61 | Forward | CCCTGCCATTGTTAAGACC |
| | SEQ ID NO: | 62 | Reverse | TGCTGCTGTTCCTGTTTTC |
| Adiponectin | SEQ ID NO: | 63 | Forward | AATGGCACACCAGGCCGTGAT |
| | SEQ ID NO: | 64 | Reverse | TCTCCAGGCTCTCCTTTCCTG |

As a result, as shown in FIGS. 10(c) and 10(d), it was confirmed that the transgenic mouse has a larger space between muscle cells compared to that of the wild-type mouse, and fat is deposited in the space. Additionally, it was confirmed that the expression of the lipogenic gene was also significantly increased.

From these results, it was confirmed that the MYH3 gene is a gene which not only affects the expression of the red muscle-related gene but also enhances the generation of intramuscular fat.

Example 4. Analysis of Genotype of MYH3 Gene

To analyze the genotype of the MYH3 gene, the 3 kb nucleotide sequence from the transcription start site (TSS) to 5'-UTR and the 1 kb nucleotide sequence from the stop codon to 3'-UTR were analyzed.

Figure 11:
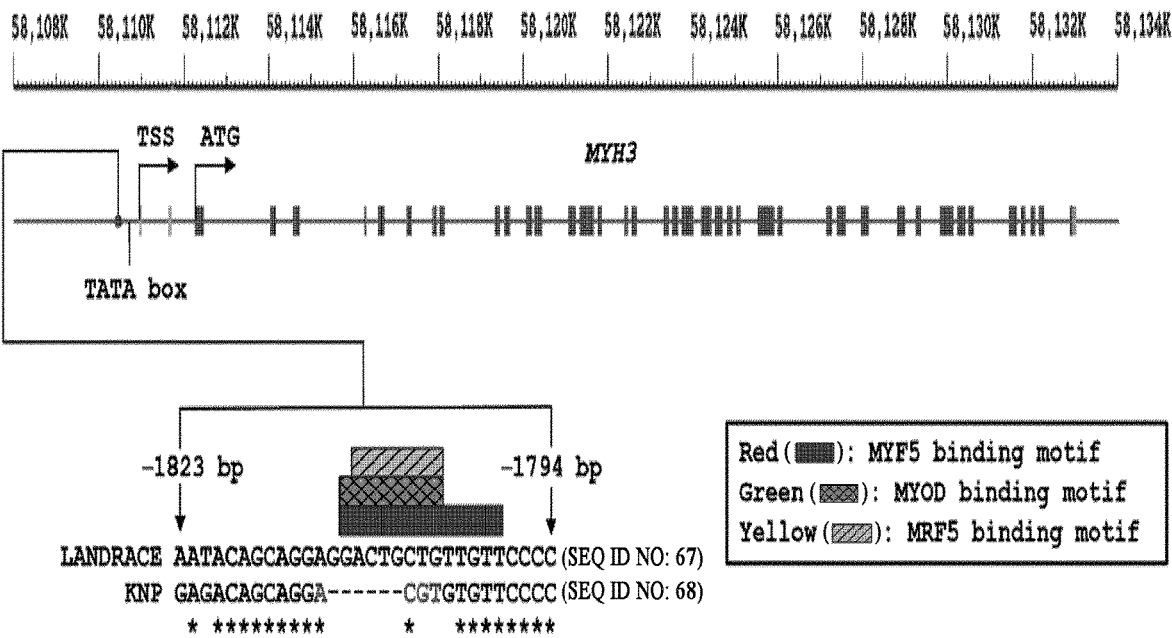
FIG. 11 shows an image illustrating the structure and quantitative trait nucleotide (QTN) of the porcine MYH3 gene.

As a result, as shown in FIG. 11, it was confirmed that MYH3-1805-1810delGGACTG (i.e., QTN) was identified in the MYH3 gene that affects meat quality (indicated by a red dot). Additionally, it was also confirmed that a nucleotide variation exists between Landrace pigs and Jeju native pigs (KNP), which is located at 5'-UTR from the start codon (ATG) in exon 3. In the case of Jeju native pigs, it was confirmed that the region between −1805 bp to −1810 bp was deleted, and this was confirmed to be a binding site of myogenesis regulatory factor (MRF).

Example 5. Determination of Breed of Pigs by Genotype Identification of MYH3 Gene As a result of confirming the presence of a nucleotide variation between the MYH3 gene of Landrace and Jeju native pigs in Example 3, an attempt was made to determine the meat quality of pigs using the nucleotide variation.

Specifically, the region containing the nucleotide variation was amplified using primers (forward: 5'-TGG TCT TTC CTA ATT GGT GAC AT-3' (SEQ ID NO: 65), and reverse: 5'-AGT TTT GAG CAA GGC TTT TGT T-3' (SEQ ID NO: 66)). PCR was performed using 100 ng/µL DNA, isolated from the blood of each of the pigs, as a template in a 10× reaction buffer containing 20 mM dNTP, 200 mM forward and reverse primers, and 1.5 units Taq DNA polymerase (TaKaRa, Japan), after adding sterile deionized water to a final volume of 25 µL. The PCR amplification was performed for a total of 30 cycles using PTC-200 (MJ Research, USA) and the primers were annealed at 60° C. The amplified product was electrophoresed on 2% agarose gel containing ethidium bromide (EtBr), and the presence of gene amplification was confirmed under UV.

Then, the "A▼CGT" region of the nucleotide sequence of the causative nucleotide variation was cleaved using the HpyCH4IV restriction enzyme. The amplified PCR product was cleaved with the restriction enzyme (HpyCH4IV). The restriction enzyme reaction was performed by mixing the PCR amplification product (3 µL), 10× buffer (1 µL), restriction enzyme (0.3 µL), and DW (5.7 µL) were mixed according to the supplier's instructions and reacted at 37° C. overnight. Electrophoresis was performed on 2% agarose gel containing ethidium bromide (EtBr) so as to confirm the cleavage patterns of Landrace and Jeju native pigs MYH3 gene by restriction enzyme.

Figure 12:
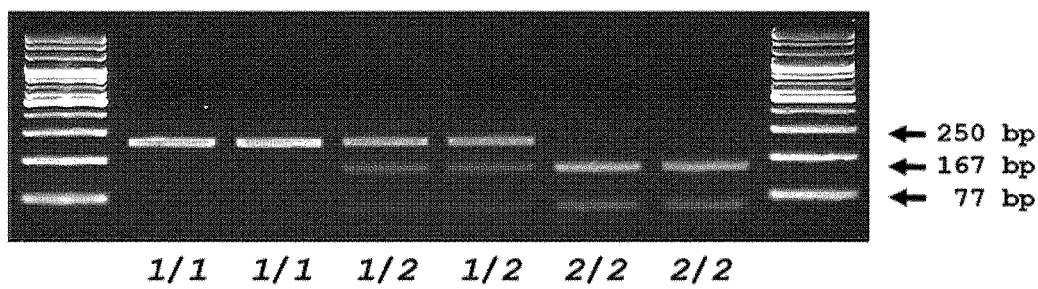
FIG. 12 shows an image illustrating the pattern of a causative nucleotide variation, which affects meat quality, cleaved by HpyCH4IV restriction enzyme, where "1/1" derived from Landrace species (q/q) shows a non-cleaved pattern, "1/2" derived from a hybridized species (q/Q) between a Landrace pig and a Jeju native pig shows a cleaved pattern, and "2/2" derived from Jeju native pigs (Q/Q) shows a cleaved pattern.

As a result, as shown in FIG. 12, it was confirmed that the MYH3 gene of Landrace pigs having poor meat quality was not cleaved and thus appeared as one band at 250 bp (1/1; a non-cleaved pattern), whereas the MYH3 gene of Jeju native pigs (KNP) was cleaved and thus appeared as two bands at 167 bp and 77 bp (2/2; a cleaved pattern). Additionally, the MYH3 gene of the hybridization breed between Landrace and Jeju native pigs appeared as two bands at 250 bp and 167 bp (1/2; a non-cleaved pattern).

From the above results, it was confirmed that the presence of the variation of MYH3 gene can be used not only for distinguishing foreign pigs from Korean native pigs but also for determining the meat quality traits of pigs.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. The scope of the present invention should be construed to include the meaning and scope of the claims to be described later and all modifications and modified forms derived from the concept of equivalents thereof rather than the detailed description of the present invention above.

What is claimed is:

1. A method for determining a meat quality trait of a pig, comprising
   (a) amplifying a polynucleotide sequence comprising nucleotides 1524-1527 of SEQ ID NO: 1, or a polynucleotide complementary thereto, from the DNA of a sample isolated from a subject pig using a primer pair consisting of nucleotide sequences of SEQ ID NOs:65 and 66;
   (b) determining the presence of MYH3-1805-1810delG-GACTG in the amplified polynucleotide sequence of the subject pig.

* * * * *

SEQUENCE LISTING

<160> NUMBER OF SEQ ID NOS: 68

<210> SEQ ID NO 1
<211> LENGTH: 3400
<212> TYPE: DNA
<213> ORGANISM: Sus scrofa

<400> SEQUENCE: 1

```
tggtggttat tgccgctgct tccaccctca gggttctcct ggcgagcgga gctccctgcc        60
tacctcggac cctcgttcca tggcccgggc aggcttcttc ccctcgtgcc ttccagcccc       120
tcatgtgcag aagcaggccg tcaggcagat gacccgagac ctcccagccg agcctctgtg       180
ctcgtggagg acgtgtgacg gagagaagga agacaggccg gctgacgggg gaaaagctgg       240
ggtgggaggc cgtcagcctt gagctcgcct tgggctcagg gatgcgacgt ggcttcacgc       300
ttgacaagaa gctcaaagaa atcctgtgtg gaaaacgtcc tctcggtgtc ccggaggtgg       360
gatggatgtg gttgtgcaga ggtgggtgaa ccggcgccaa ctaaaggtca aaagcaagcc       420
ggccccaacc gcggcccctg gtgtttaaga agggaccgcc agcacccttc ccctgaccac       480
ccagcacacg tcacagcctg agacgtagcc agggcccctg cactgtccct cagcccagg       540
gggcttgcta acacctctgc ttccaggtga catgcacctg tcctcaccag gcctcccagg       600
atggctggcc aatggcgcag agagtcaggc cggcgcgtcc ctgggcaggg agaccacgcc       660
ccttcaggac cggagggtcc ttgaggaggg tcgagctctc ttcttggacg aggaggattt       720
ctggggggagg gggtttcagt cccagcggcg ggggtgggc ggtggggcgt gacatgtagc       780
atggcaggtc catgcttcct gactttcctc ctgatggcca cttgcctacc tgctttgatc       840
taaaaatcac caaatctca gacataatcg agtcaccatt tatccaagaa accatcgagg       900
gtaaagccgc agcttccatt tctttcgatt cttcttccag ggttctgcct tgggcccagc       960
atgcagtggg tgtttaatta atgccctgc ccctcgggga ctgcagcccc actccccctg      1020
ccccaccccc agcccttaga gtggcctcct ggcccgcgct gcgtgtggct atgctgggag      1080
ggggccgttc ttattctcca gtggggacag ctgacaccag aatgaacgac aacgggttac      1140
ccacaggcca cgctcccaac ggtctgtcag ggaaaaaaag ggaaaaacag acataaagtg      1200
gaataagaat gggcaaacgc ttcagccata cccctctgtg ctcctaaggc tttatttttc      1260
taaccctgat ttagaaacag ccatgctcgt tagacgcccc ctcacccccc tttctctgca      1320
ggccctgcca tcccccacc cccgcccgg ccagcagctg gtcttttccta attggtgaca      1380
tgtcttaata actacaggtc cttgagcagc tgtcactgtg gctcctggct ggtgggctac      1440
ctccctctca gtcatttact cgttggtcct actggcgctt aagacagagg tttagttaat      1500
gacgatccta atgagacagc aggacgtgtg ttccccacac aagttgtaca atcacacatt      1560
cctgccacaa ccctgtgttg taacaaaagc cttgctcaaa actccaagag ggtttaaact      1620
tttccgtcct tggcttcatc cctttgccca caggccgaga ttctaggtcc ccgctgtccc      1680
agagaccagg ctcatctcca gccgtgtggc gcctgtggga tggagcgagg gcccccggca      1740
aggctgtccc atcactgagc cgccggttca gagaaaggca tcccaaactt ccagcttttct      1800
ccagctagga tcctgtcatt tctatatata cctctctctt ggcagcggca aaaaaaagcg      1860
aggaaggagc tggtcctcac ttgtggtgtc ggtcactctc tttccaaata tagagaagga      1920
atgagtggcg ggggttagca ggggctataa aagcccgcgg ggagcgcccc ttgtagctgc      1980
tctgtgggcg gaggagagtc acagtgcccc ttgtgcgggt ccttcccatc tgaggctcag      2040
aggctcgtgt ggccctgccc ggcttttggta aggaccagac gtgcggctga ttctcagccc      2100
ctccccgcct ccagcatccc gcttccttca cctgttctcc cctgccctca tcctccagag      2160
ccttcccggg cagggtccct tcggatgctc tgtggaccac tgccgtcacc ccggcccatg      2220
aacgctgcca cctctctgac ttgtgcagag gccagtgggc ctggccgcct ccccacctgc      2280
```

```
gctgcgggcc tgcggtgtct gtcctctcaa ggccacgctg gctgtgcatc cgttggcttg    2340
tctgagactt cgccctgcct gcccacagaa gacaggggc ctggccctgg cttggaggca    2400 caggctttc aaacagagct tctgtcctga ctgctcacat ctgaggagga ggcatggcag    2460
acagagggtg gtgccacccg ggcaggaggg agccaggtct ggggcggctg ggggctctcc    2520
tgccttcagg gctcacctgt gggccaggtc ccatttgctc ctccagcttg tctctgggcc    2580
aaggctcttt taaagttatt cgtcctttct cttcatttgg ttaattgatt aaggcccatt    2640
cagaactgaa ccagacactc ccacgtctcc tgacctttg tgtatttatt gcaggtctga    2700
tttctcacgg ctgctgctgt ctgctgtcct cctgcgggtg tgactctcag gtgagaaagc    2760
aggtcaggtc ccctggctca gccatctcca gggtactggt tcccccccgg ccacggcctt    2820
gcggcgagca ggacaggtta ggctggagag gagcccagg gaaggctgcc aagcagatgc    2880
tgatgtgaga agccgcttgt tgtagaagg gactgaagcc ggtttccagg tggggatgg    2940 agccaccctg aatccgagcg gttccaaaac tccttagcta tttgcccttt aacacgctct    3000
ttgaagaatg tttgctttg agagtgttta cctttacgtc ttccctcagc aaccctggc    3060 ttttacagaa gaggaaagcg gggtcccaag agctgcaccc acctctgggc gctctgcccg    3120
ccccagcccc ggctaacggg ggagcttgga ttgcgtgcat cccgtgtcct ctgcacagag    3180
gagctgctca atgaaatgca cccatttgat cccggggggc tggatggcgg cggccttgct    3240
cctgggctcc gcctggaggg cgcctgtggg gtcagggctg gagtctggcc cggggactca    3300 ctgggggtc ccttccagcc gacaccatga gcagcgacac tgaaatggaa gtgttcggca    3360
tagccgctcc cttcctccgc aagtcggaaa aggagaggat                            3400

<210> SEQ ID NO 2
<211> LENGTH: 12238
<212> TYPE: DNA
<213> ORGANISM: Artificial Sequence
<220> FEATURE:
<223> OTHER INFORMATION: CAGGS-MYH3-Flag vector

<400> SEQUENCE: 2
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atgggtcgag gtgagcccca cgttctgctt cactctcccc     420
atctcccccc cctccccacc cccaattttg tatttattta ttttttaatt attttgtgca     480
gcgatggggg cgggggggg ggggcgcgc gccaggcggg gcgggcggg gcgaggggcg     540 gggcggggcg aggcggagag gtgcggcggc agccaatcag agcggcgcgc tccgaaagtt     600
tccttttatg gcgaggcggc ggcggcggcg gccctataaa aagcgaagcg cgcggcgggc     660
gggagtcgct gcgttgcctt cgccccgtgc cccgctccgc gccgcctcgc gccgcccgcc     720
ccggctctga ctgaccgcgt tactcccaca ggtgagcggg cgggacggcc cttctcctcc     780
gggctgtaat tagcgcttgg tttaatgacg gctcgtttct tttctgtggc tgcgtgaaag     840
ccttaaaggg ctccgggagg gccctttgtg cgggggggag cggctcgggg ggtgcgtgcg     900
tgtgtgtgtg cgtggggagc gccgcgtgcg gcccgcgctg cccggcggct gtgagcgctg     960
```

```
cggggcgcggc gcggggcttt gtgcgctccg cgtgtgcgcg aggggagcgc ggccggggc    1020
ggtgccccgc ggtgcggggg ggctgcgagg ggaacaaagg ctgcgtgcgg ggtgtgtgcg    1080
tggggggtg agcaggggt gtgggcgcgg cggtcgggct gtaacccccc cctgcaccccc    1140
cctccccgag ttgctgagca cggcccggct tcgggtgcgg ggctccgtgc ggggcgtggc    1200
gcggggctcg ccgtgccggg cggggggtgg cggcaggtgg gggtgccggg cggggcgggg    1260
ccgcctcggg ccggggaggg ctcggggag gggcgcggcg gccccggagc gccggcggct    1320
gtcgaggcgc ggcgagccgc agccattgcc ttttatggta atcgtgcgag agggcgcagg    1380
gacttccttt gtcccaaatc tggcggagcc gaaatctggg aggcgccgcc gcaccccctc    1440
tagcgggcgc gggcgaagcg gtgcggcgcc ggcaggaagg aaatgggcgg ggagggcctt    1500
cgtgcgtcgc cgcgccgccg tccccttctc catctccagc ctcggggctg ccgcaggggg    1560
acggctgcct tcgggggga cggggcaggg cggggttcgg cttctggcgt gtgaccggcg    1620
gctctagagc caccatgagc agcgacactg aaatggaagt gttcggcata gccgctccct    1680
tcctccgcaa gtcggaaaag gagaggatcg aggcgcagaa ccagcccttc gatgccaaaa    1740
cctactgctt cgtggtcgac tcgaaggaag agtacgccaa ggggaaaatt aagagcaccc    1800
aggatgggaa ggtcacggtg gagaccgaag acaacaggac cctggtggtg aagccggagg    1860
atgtgtatgc catgaacccc cccaagtttg accggatcga ggacatggcc atgctgacgc    1920
acctgaacga gccggccgtg ctgtacaacc tcaaggaccg gtacacctcc tggatgatct    1980
atacctactc gggcctcttc tgtgtcaccg tcaaccccta caagtggctg ccggtgtaca    2040
accccgaggt ggtggagggc taccgaggca aaaagcgcca ggaggccccg ccccacatct    2100
tctccatctc cgacaacgcc tatcagttca tgttgacaga tcgtgaaaac cagtccattc    2160
tgatcaccgg agaatccggg gcgggaaaga ctgtgaacac caagagggtc atccagtact    2220
ttgcaacaat tgctgccact ggggacctcg ccaagaagaa ggactccaag atgaagggga    2280
ctctggagga ccagatcatc agcgccaacc cgctgctgga ggccttcggc aacgccaaga    2340
ccgtgaggaa cgacaactcg tcccgcttcg gcaagttcat ccgaatccat tttggtacca    2400
ccgggaagct ggcctccgca gacatcgaaa catatctgct cgaaaaatcg agagtgacct    2460
tccagctgaa ggctgagagg agctaccaca tcttctacca gattctctcc aacaagaagc    2520
cggagctcat agagctgctg ctcattacaa ccaacccctt cgactacccg ttcatcagcc    2580
agggcgagat cctcgtggcc agcattgatg atgccgagga gctgctagcc acggatagtg    2640
ccatcgacat cctgggcttc acccccagagg agaaatctgg actctacaag ctgacgggcg    2700
ccgtgatgca ctacgggaac atgaagttca gcagaagca acgggaggag caggcagagc    2760
cggacggcac ggaagtggct gacaagacag cctacctcat gggcctgaac tcttcggacc    2820
tcctgaaggc tttgtgcttc cccagagtca agttgggaa cgagtatgtt accaagggcc    2880
agaccgtgga tcaggtgcac cacgcggtga acgcactctc caaatccgtc tacgagaagc    2940
tcttcctgtg gatggtcacc cgcatcaacc agcagctgga caccaagctg cccaggcagc    3000
acttcatcgg cgtcttggac atcgcgggct tgagatcttt tgagtataac agcctggagc    3060
agctgtgcat caacttcacc aacgagaaac tgcaacagtt tttcaaccac cacatgttcg    3120
tgctggagca ggaggagtac aagaaggaag gcatcgagtg gacgttcatc gacttcggga    3180
tggacctggc cgcctgcatc gagctcatcg agaagcccat gggcatcttc tccatcctgg    3240
aggaggagtg catgttcccc aaggccacag acacctcctt caagaacaag ctctatgacc    3300
```

```
agcacctggg caagtctgcc aacttccaga agcccaaggt gctcaagggc agggccgagg   3360
cccacttctc cctgatccac tacgcgggca ccgtggacta cagtgtctcg ggctggctgg   3420
agaagaacaa ggaccccctg aacgagacgg tggtcgggct gtaccagaag tcctccaacc   3480
ggctcctggc gcacctctac gcgacctttcg ccacggccga cgctgacagc ggaaagaaga   3540
aagttgccaa gaaaaagggt tcttccttcc aaaccgtctc tgcccttttc agggaaaacc   3600
tgaacaagct gatgtcgaat ttaaggacga ctcaccctca ctttgtgcgc tgtatcattc   3660
ccaatgaaac caaaccccca ggggccatgg aacatagcct ggtcctgcac cagctgaggt   3720
gtaacgcgt gctggagggc atccgcatct gcaggaaggg cttccccaat cggatcctct   3780
acggggattt taaacaaaga taccgcgtgc tgaatgccag cgccatcccc gagggacagt   3840
tcatcgacag caagaaggcg tgtgaaaagc tgttggcgtc catcgatatt gaccacactc   3900
agtacaaatt cggacacacc aaggtgttct tcaaggccgg cttgctggga accctggagg   3960
aaatgcggga cgaccgcctg gccaagctca tcacccggac gcaagccgtg tgcaggggct   4020
tcctcatgcg cgtggaattc cagaagatgg tgcagagaag ggagtccatc ttctgcatcc   4080
agtacaacat ccgagccttc atgaacgtca gcactggcc ctggatgaaa ctcttcttca   4140
agatcaagcc tctgctgaag agcgcagaga ccgagaagga gatggccacc atgaaggagg   4200
agttccagaa aaccaaggag gaactcgcca gtcagaggc aaagaggaag gaactggagg   4260
aaaagatggt gactctggta caagagaaga acgacctgca gctccaagta caagctgaaa   4320
gtgaaaactt gttggatgca gaggaaagat gtgaccagct gatcaaagcc aagtttcagc   4380
tggaggccaa aatcaaggag gtgactgaga gagctgagga tgaggaagag atcaatgccg   4440
agctgacggc caagaagagg aaactggagg atgagtgctc agaactgaag aaagacatcg   4500
atgaccttga gctgacactg gccaaggttg aaaaggagaa acatgccaca gagaacaagg   4560
ttaaaaacct tactgaggaa ctggccggct tggatgaaac cattgcgaag ttgaccaggg   4620
agaagaaggc cctccaggag gcccaccagc agacccttga tgacctccaa gctgaagagg   4680
acaaagtcaa ctccttaagc aaaatcaaga gcaaactgga acagcaggtg gacgatctgg   4740
aaagctccct agaacaagag aagaagctcc gggtcgacct ggaaaggaat aaaaggaagc   4800
ttgagggtga cttgaagctt gcccaggagt ccatactgga tctggagaat gacaagcaac   4860
agctggatga aaggctcaag aagaaggatt ttgagtccag tcagctgcag agcaaagtgg   4920
aagatgagca gacccctgggc ctccagtttc agaagaaaat taaagagctc caggctcgaa   4980
tcgaggagct ggaggaagag attgaggccg agagggccac ccgcgccaag acggagaagc   5040
agcgcagcga ctacgcccgg gagctggagg agctgagcga gcggctggag gaggcggggg   5100
gcgtcacatc cacgcagatc gagctgaaca agaagcgcga ggccgagttc ctgaagctgc   5160
gccgggacct ggaggaggcc accctgcagc acagaggcca agtggctgcg ctgaggaaga   5220
agcacgcgga cagcgtggct gagctggggg agcagatcga caacctgcag agggtcaagc   5280
agaagctgga gaaggagaag agcgaattca gctggagct ggacgacctg ccggcaacg   5340
tggagagcgt gtccaaggcg aaggccaacc tggaaaaaat ctgccgcacc ctggaggatc   5400
agctaagcga ggccaggggc aagaacgagg aaatccagag gagcatgagc gagctgacca   5460
tgcagaagtc ccgtcttcag acggaggccg gtgagctgag tcgtcaactc gaagagaaag   5520
agagcacagt atcacagctt tccagaagca agcaagcgtt tacccagcaa atagaagagc   5580
tcaagagggca gctggaggag gagagcaagg ccaagaacgc cctggcgcac gccctgcagt   5640
cctcccgcca cgactgcgac ctgctgcggg aacagtatga ggaggagcag gaagccaagg   5700
```

```
ccgagctgca gagggcgctg tccaaggcca acagcgaggt tgcccagtgg aggaccaagt    5760
acgagacgga cgccatccag cgcacggagg agctggagga ggccaagaaa aagcttgctc    5820
agcgccttca ggattccgag gagcaggtgg aggcagtgaa cgccaagtgt gcctccctgg    5880
agaagaccaa gcagaggctg caagcggagg tggaggacct gatggtggac gtggacagag    5940
ccaactctct ggctgctgcg ctggacaaga agcagagaaa cttcgacaag gtgctcgccg    6000
agtggaaaac aaagtgtgag gagagccagg cagagctgga ggcagctctg aaggaatccc    6060
gctccttgag caccgagctc ttcaagctga aaaatgccta cgaagaagcc ttagatcaac    6120
ttgaaactgt gaagcgagaa aataagaact tggagcagga gatagcagat ctcacagaac    6180
aaattgctga gaacggtaaa accatccatg aactggagaa atcaagaaag cagatcgagc    6240
tggagaaggc tgatatccag ctggctcttg aggaagcaga ggccgccctt gagcacgaag    6300
aggccaagat cctccgaatc cagctggaac tgacccaggt gaaatcggaa atcgacagga    6360
agatggctga gaaagacgaa gagatcgagc agctcaagag gaactaccag agaaccgtgg    6420
agacgatgca gagcgccttg gacgccgagg tgcggagccg caacgaggcc atcaggatca    6480
agaagaagat ggagggggac ctgaacgaga tcgagatcca gctgagccac gccaaccgcc    6540
aggccgcgga gaccctcaaa cacctccggg gcgtccaagg acagctgaag gacacccagc    6600
tccacctgga cgacgctctc cgaggccagg aggacctgaa ggagcagctg gccatcgtgg    6660
agcgcagagc cagcctgctg caggccgagg tggaggagct gcgggcctcc ctggagcaga    6720
cggagagggc ccggaaactg gcagagcagg agctcctgga cgccaacgag agggtgcagc    6780
tgctccacac ccagaacacc agcctcatcc acaccaagaa gaagctggag acggacctga    6840
tgcagctcca gagcgaggtc gaggacgcca gcagggatgc gaggaacgcc gaggagaagg    6900
cgaagaaggc caccaccgac gcggccatga tggccgagga gctgaagaag gagcaggaca    6960
ccagcgccca cctggagcgg atgaagaaga acctggagca gacggtgaag gacctgcagc    7020
accgcctgga cgaggcggaa cagttggccc tgaagggcgg gaagaagcag atccagaagc    7080
tggaggccag aatccgagag ctggagtttg agcttgaggg ggagcagaag aagaacacgg    7140
agtctgtcaa gggcctcagg aaatacgagc ggcgggtcaa ggagttaact taccagagtg    7200
aagaggacag gaagaatgtg ctgagattac aggacctggt ggacaaactt caagcgaagg    7260
tcaagtccta caagaggcag gcggaggagg ctgatgaaca agccaatgct catctcacca    7320
agttccgaaa agctcagcat gagctcgagg aggctgaaga acgggctgat atcgccgaat    7380
ctcaggtcaa taagcttcgc gcaaagaccc gagacttcac ctccagccgg atggtggtcc    7440
atgagagcga agaggattac aaggatgacg acgataagtg agaattcact cctcaggtgc    7500
aggctgccta tcagaaggtg gtggctggtg tggccaatgc cctggctcac aaataccact    7560
gagatctttt tccctctgcc aaaaattatg gggacatcat gaagcccctt gagcatctga    7620
cttctggcta taaaggaaa tttattttca ttgcaatagt gtgttggaat ttttttgtgtc    7680
tctcactcgg aaggacatat gggagggcaa atcatttaaa acatcagaat gagtatttgg    7740
tttagagttt ggcaacatat gccatatgct ggctgccatg aacaaaggtg gctataaaga    7800
ggtcatcagt atatgaaaca gcccctgct gtccattcct tattccatag aaaagccttg    7860
acttgaggtt agatttttt tatattttgt tttgtgttat tttttctttt aacatccta    7920
aaatttttcct tacatgtttt actagccaga ttttcctcc tctcctgact actcccagtc    7980
atagctgtcc ctcttctctt atgaagatcc ctcgacctgc agttgggggtt gcgccttttc    8040
```

-continued

```
caaggcagcc ctgggtttgc gcagggacgc ggctgctctg ggcgtggttc cgggaaacgc    8100
agcggcgccg accctgggtc tcgcacattc ttcacgtccg ttcgcagcgt caccggatc     8160 ttcgccgcta cccttgtggg cccccggcg acgcttcctg ctccgcccct aagtcgggaa    8220
ggttccttgc ggttcgcggc gtgccggacg tgacaaacgg aagccgcacg tctcactagt    8280
accctcgcag acggacagcg ccagggagca atggcagcgc gccgaccgcg atgggctgtg    8340
gccaatagcg gctgctcagc agggcgcgcc gagagcagcg gccgggaagg ggcggtgcgg    8400 gaggcgggt gtgggcggt agtgtgggcc ctgttcctgc ccgcgcggtg ttccgcattc     8460
tgcaagcctc cggagcgcac gtcggcagtc ggctccctcg ttgaccgaat caccgacctc    8520
tctccccagg gggatccacc ggagcttacc atgaccgagt acaagcccac ggtgcgcctc    8580 gccaccgcg acgacgtccc cagggccgta cgcaccctcg ccgccgcgtt cgccgactac     8640
cccgccacgc gccacaccgt cgatccggac cgccacatcg agcgggtcac cgagctgcaa    8700
gaactcttcc tcacgcgcgt cgggctcgac atcggcaagg tgtgggtcgc ggacgacggc    8760
gccgcggtgg cggtctggac cacgccgag agcgtcgaag cggggcggt gttcgccgag     8820 atcggcccgc gcatggccga gttgagcggt tcccggctgg ccgcgcagca acagatggaa    8880
ggcctcctgg cgccgcaccg gcccaaggag cccgcgtggt tcctggccac cgtcggcgtc    8940
tcgcccgacc accagggcaa gggtctgggc agcgccgtcg tgctccccgg agtggaggcg    9000
gccgagcgcg ccggggtgcc cgccttcctg gagacctccg cgccccgcaa cctcccttc     9060 tacgagcggc tcggcttcac cgtcaccgcc gacgtcgagg tgcccgaagg accgcgcacc    9120
tggtgcatga cccgcaagcc cggtgcctga cgcccgcccc acgacccgca gcgcccgacc    9180
gaaaggagcg cacgaccca tgcatcggta cctttaagac caatgactta caaggcagct    9240
gtagatctta gccactttt aaagaaaag ggggactgg aagggctaat tcactcccaa      9300
cgaagacaag atctgctttt tgcttgtact gggtctctct ggttagacca gatctgagcc    9360
tgggagctct ctggctaact agggaaccca ctgcttaagc ctcaataaag cttgccttga    9420
gtgcttcaag tagtgtgtgc ccgtctgttg tgtgactctg gtaactagag atccctcaga    9480
cccttttagt cagtgtggaa aatctctagc agtagtagtt catgtcatct tattattcag    9540
tatttataac ttgcaaagaa atgaatatca gagagtgaga ggaacttgtt tattgcagct    9600
tataatggtt acaaataaag caatagcatc acaaatttca caaataaagc attttttca     9660 ctgcattcta gttgtggttt gtccaaactc atcaatgtat cttatcatgt ctgctgcagc    9720
ccaagcttgg cgtaatcatg gtcatagctg tttcctgtgt gaaattgtta tccgctcaca    9780
attccacaca acatacgagc cggaagcata aagtgtaaag cctggggtgc ctaatgagtg    9840
agctaactca cattaattgc gttgcgctca ctgcccgctt ccagtcggga aacctgtcg     9900 tgccagcgga tccgcatctc aattagtcag caaccatagt cccgcccta actccgccca    9960 tcccgcccct aactccgccc agttccgccc attctccgcc ccatggctga ctaatttttt   10020
ttatttatgc agaggccgag gccgcctcgg cctctgagct attccagaag tagtgaggag   10080 gctttttgg aggcctaggc ttttgcaaaa agctaacttg tttattgcag cttataatgg    10140
ttacaaataa agcaatagca tcacaaattt cacaaataaa gcatttttt cactgcattc    10200 tagttgtggt ttgtccaaac tcatcaatgt atcttatcat gtctggatcc gctgcattaa   10260
tgaatcggcc aacgcgcggg gagaggcggt ttgcgtattg ggcgctcttc cgcttcctcg   10320
ctcactgact cgctgcgctc ggtcgttcgg ctgcggcgag cggtatcagc tcactcaaag   10380
gcggtaatac ggttatccac agaatcaggg gataacgcag gaaagaacat gtgagcaaaa   10440
```

```
ggccagcaaa aggccaggaa ccgtaaaaag gccgcgttgc tggcgttttt ccataggctc   10500
cgcccccctg acgagcatca caaaaatcga cgctcaagtc agaggtggcg aaacccgaca   10560
ggactataaa gataccaggc gtttccccct ggaagctccc tcgtgcgctc tcctgttccg   10620
accctgccgc ttaccggata cctgtccgcc tttctccctt cgggaagcgt ggcgctttct   10680
caatgctcac gctgtaggta tctcagttcg gtgtaggtcg ttcgctccaa gctgggctgt   10740
gtgcacgaac ccccgttca gcccgaccgc tgcgccttat ccgtaactat cgtcttgag   10800 tccaacccgg taagacacga cttatcgcca ctggcagcag ccactggtaa caggattagc   10860
agagcgaggt atgtaggcgg tgctacagag ttcttgaagt ggtggcctaa ctacggctac   10920
actagaagga cagtatttgg tatctgcgct ctgctgaagc cagttacctt cggaaaaaga   10980
gttggtagct cttgatccgg caaacaaacc accgctggta gcggtggttt ttttgtttgc   11040
aagcagcaga ttacgcgcag aaaaaaagga tctcaagaag atcctttgat cttttctacg   11100
gggtctgacg ctcagtggaa cgaaaactca cgttaaggga ttttggtcat gagattatca   11160
aaaaggatct tcacctagat ccttttaaat taaaaatgaa gttttaaatc aatctaaagt   11220
atatatgagt aaacttggtc tgacagttac caatgcttaa tcagtgaggc acctatctca   11280
gcgatctgtc tatttcgttc atccatagtt gcctgactcc ccgtcgtgta gataactacg   11340
atacgggagg gcttaccatc tggccccagt gctgcaatga taccgcgaga cccacgctca   11400
ccggctccag atttatcagc aataaaccag ccagccggaa gggccgagcg cagaagtggt   11460
cctgcaactt tatccgcctc catccagtct attaattgtt gccgggaagc tagagtaagt   11520
agttcgccag ttaatagttt gcgcaacgtt gttgccattg ctacaggcat cgtggtgtca   11580
cgctcgtcgt ttggtatggc ttcattcagc tccggttccc aacgatcaag gcgagttaca   11640
tgatccccca tgttgtgcaa aaaagcggtt agctccttcg gtcctccgat cgttgtcaga   11700
agtaagttgg ccgcagtgtt atcactcatg gttatggcag cactgcataa ttctcttact   11760
gtcatgccat ccgtaagatg cttttctgtg actggtgagt actcaaccaa gtcattctga   11820
gaatagtgta tgcggcgacc gagttgctct tgcccggcgt caatacggga taataccgcg   11880
ccacatagca gaactttaaa agtgctcatc attggaaaac gttcttcggg gcgaaaactc   11940
tcaaggatct taccgctgtt gagatccagt tcgatgtaac ccactcgtgc acccaactga   12000
tcttcagcat cttttacttt caccagcgtt tctgggtgag caaaaacagg aaggcaaaat   12060
gccgcaaaaa agggaataag ggcgacacgg aaatgttgaa tactcatact cttccttttt   12120
caatattatt gaagcattta tcagggttat tgtctcatga gcggatacat atttgaatgt   12180
atttagaaaa ataaacaaat aggggttccg cgcacatttc cccgaaaagt gccacctg    12238
```

<210> SEQ ID NO 3
<211> LENGTH: 21
<212> TYPE: DNA
<213> ORGANISM: Artificial Sequence
<220> FEATURE:
<223> OTHER INFORMATION: pMYH3 F-primer

<400> SEQUENCE: 3
aaaagctcag catgagctcg a                                             21

<210> SEQ ID NO 4
<211> LENGTH: 21
<212> TYPE: DNA
<213> ORGANISM: Artificial Sequence
<220> FEATURE:

<223> OTHER INFORMATION: pMYH3 R-primer

<400> SEQUENCE: 4
agggtcagga accatgaaaa t                                        21

<210> SEQ ID NO 5
<211> LENGTH: 19
<212> TYPE: DNA
<213> ORGANISM: Artificial Sequence
<220> FEATURE:
<223> OTHER INFORMATION: pMYH1 F-primer

<400> SEQUENCE: 5
gttctgaaga gggtggtac                                           19

<210> SEQ ID NO 6
<211> LENGTH: 18
<212> TYPE: DNA
<213> ORGANISM: Artificial Sequence
<220> FEATURE:
<223> OTHER INFORMATION: pMYH1 R-primer

<400> SEQUENCE: 6
agatgcggat gccctcca                                            18

<210> SEQ ID NO 7
<211> LENGTH: 19
<212> TYPE: DNA
<213> ORGANISM: Artificial Sequence
<220> FEATURE:
<223> OTHER INFORMATION: pMYH2 F-primer

<400> SEQUENCE: 7
gggctcaaac tggtgaagc                                           19

<210> SEQ ID NO 8
<211> LENGTH: 18
<212> TYPE: DNA
<213> ORGANISM: Artificial Sequence
<220> FEATURE:
<223> OTHER INFORMATION: pMYH2 R-primer

<400> SEQUENCE: 8
agatgcggat gccctcca                                            18

<210> SEQ ID NO 9
<211> LENGTH: 20
<212> TYPE: DNA
<213> ORGANISM: Artificial Sequence
<220> FEATURE:
<223> OTHER INFORMATION: pMYH13 F-primer

<400> SEQUENCE: 9
cacagggctc tggccgacat                                          20

<210> SEQ ID NO 10
<211> LENGTH: 20
<212> TYPE: DNA
<213> ORGANISM: Artificial Sequence
<220> FEATURE:
<223> OTHER INFORMATION: pMYH13 R-primer

<400> SEQUENCE: 10
cgtgcgcaca ggggtgtagt                                          20

```
<210> SEQ ID NO 11
<211> LENGTH: 21
<212> TYPE: DNA
<213> ORGANISM: Artificial Sequence
<220> FEATURE:
<223> OTHER INFORMATION: pADPRM F-primer

<400> SEQUENCE: 11
catcctgaga ccgtgccttc a                                            21

<210> SEQ ID NO 12
<211> LENGTH: 20
<212> TYPE: DNA
<213> ORGANISM: Artificial Sequence
<220> FEATURE:
<223> OTHER INFORMATION: pADPRM R-primer

<400> SEQUENCE: 12
ttccgcattt gggttgtgct                                              20

<210> SEQ ID NO 13
<211> LENGTH: 20
<212> TYPE: DNA
<213> ORGANISM: Artificial Sequence
<220> FEATURE:
<223> OTHER INFORMATION: pSCO1 F-primer

<400> SEQUENCE: 13
tcctcacgga ctcggggttt                                              20

<210> SEQ ID NO 14
<211> LENGTH: 20
<212> TYPE: DNA
<213> ORGANISM: Artificial Sequence
<220> FEATURE:
<223> OTHER INFORMATION: pSCO1 R-primer

<400> SEQUENCE: 14
gtggggtctc tgctgccctt                                              20

<210> SEQ ID NO 15
<211> LENGTH: 20
<212> TYPE: DNA
<213> ORGANISM: Artificial Sequence
<220> FEATURE:
<223> OTHER INFORMATION: pTMEM220 F-primer

<400> SEQUENCE: 15
cccagacgca gaactgtggg                                              20

<210> SEQ ID NO 16
<211> LENGTH: 20
<212> TYPE: DNA
<213> ORGANISM: Artificial Sequence
<220> FEATURE:
<223> OTHER INFORMATION: pTMEM220 R-primer

<400> SEQUENCE: 16
gttgtatgcc aagccggcag                                              20

<210> SEQ ID NO 17
<211> LENGTH: 20
<212> TYPE: DNA
<213> ORGANISM: Artificial Sequence
<220> FEATURE:
<223> OTHER INFORMATION: pENSSSCG00000029441 F-primer
```

<400> SEQUENCE: 17
tcgtgctgga gcaggaggag　　　　　　　　　　　　　　　　　　　　　　　20

<210> SEQ ID NO 18
<211> LENGTH: 20
<212> TYPE: DNA
<213> ORGANISM: Artificial Sequence
<220> FEATURE:
<223> OTHER INFORMATION: pENSSSCG00000029441 R-primer

<400> SEQUENCE: 18
aggtgtctgt ggccttgggg　　　　　　　　　　　　　　　　　　　　　　　20

<210> SEQ ID NO 19
<211> LENGTH: 20
<212> TYPE: DNA
<213> ORGANISM: Artificial Sequence
<220> FEATURE:
<223> OTHER INFORMATION: pENSSSCG00000018006 F-primer

<400> SEQUENCE: 19
agaaccagcc cttcgatgcc　　　　　　　　　　　　　　　　　　　　　　　20

<210> SEQ ID NO 20
<211> LENGTH: 20
<212> TYPE: DNA
<213> ORGANISM: Artificial Sequence
<220> FEATURE:
<223> OTHER INFORMATION: pENSSSCG00000018006 R-primer

<400> SEQUENCE: 20
tggcatacac atcctccggc　　　　　　　　　　　　　　　　　　　　　　　20

<210> SEQ ID NO 21
<211> LENGTH: 20
<212> TYPE: DNA
<213> ORGANISM: Artificial Sequence
<220> FEATURE:
<223> OTHER INFORMATION: pGAPDH F-primer

<400> SEQUENCE: 21
gggcatgaac catgagaagt　　　　　　　　　　　　　　　　　　　　　　　20

<210> SEQ ID NO 22
<211> LENGTH: 20
<212> TYPE: DNA
<213> ORGANISM: Artificial Sequence
<220> FEATURE:
<223> OTHER INFORMATION: pGAPDH R-primer

<400> SEQUENCE: 22
gggcatgaac catgagaagt　　　　　　　　　　　　　　　　　　　　　　　20

<210> SEQ ID NO 23
<211> LENGTH: 18
<212> TYPE: DNA
<213> ORGANISM: Artificial Sequence
<220> FEATURE:
<223> OTHER INFORMATION: pMYH3 F-primer

<400> SEQUENCE: 23
ccgagagctg gagtttga　　　　　　　　　　　　　　　　　　　　　　　　18

<210> SEQ ID NO 24
<211> LENGTH: 21

```
<212> TYPE: DNA
<213> ORGANISM: Artificial Sequence
<220> FEATURE:
<223> OTHER INFORMATION: pMYH3 R-primer

<400> SEQUENCE: 24
ctcccatatg tccttccgag t                                       21

<210> SEQ ID NO 25
<211> LENGTH: 20
<212> TYPE: DNA
<213> ORGANISM: Artificial Sequence
<220> FEATURE:
<223> OTHER INFORMATION: Myh7 F-primer

<400> SEQUENCE: 25
agtcccaggt caacaagctg                                         20

<210> SEQ ID NO 26
<211> LENGTH: 20
<212> TYPE: DNA
<213> ORGANISM: Artificial Sequence
<220> FEATURE:
<223> OTHER INFORMATION: Myh7 R-primer

<400> SEQUENCE: 26
ttccacctaa agggctgttg                                         20

<210> SEQ ID NO 27
<211> LENGTH: 20
<212> TYPE: DNA
<213> ORGANISM: Artificial Sequence
<220> FEATURE:
<223> OTHER INFORMATION: Myh2 F-primer

<400> SEQUENCE: 27
agtcccaggt caacaagctg                                         20

<210> SEQ ID NO 28
<211> LENGTH: 20
<212> TYPE: DNA
<213> ORGANISM: Artificial Sequence
<220> FEATURE:
<223> OTHER INFORMATION: Myh2 R-primer

<400> SEQUENCE: 28
gcatgaccaa aggtttcaca                                         20

<210> SEQ ID NO 29
<211> LENGTH: 20
<212> TYPE: DNA
<213> ORGANISM: Artificial Sequence
<220> FEATURE:
<223> OTHER INFORMATION: Myh1 F-primer

<400> SEQUENCE: 29
agtcccaggt caacaagctg                                         20

<210> SEQ ID NO 30
<211> LENGTH: 21
<212> TYPE: DNA
<213> ORGANISM: Artificial Sequence
<220> FEATURE:
<223> OTHER INFORMATION: Myh1 R-primer

<400> SEQUENCE: 30
```
cacattttgc tcatctcttt g                                      21

<210> SEQ ID NO 31
<211> LENGTH: 20
<212> TYPE: DNA
<213> ORGANISM: Artificial Sequence
<220> FEATURE:
<223> OTHER INFORMATION: Myh4 F-primer

<400> SEQUENCE: 31
agtcccaggt caacaagctg                                        20

<210> SEQ ID NO 32
<211> LENGTH: 22
<212> TYPE: DNA
<213> ORGANISM: Artificial Sequence
<220> FEATURE:
<223> OTHER INFORMATION: Myh4 R-primer

<400> SEQUENCE: 32
tttctcctgt cacctctcaa ca                                     22

<210> SEQ ID NO 33
<211> LENGTH: 20
<212> TYPE: DNA
<213> ORGANISM: Artificial Sequence
<220> FEATURE:
<223> OTHER INFORMATION: Myoglobin F-primer

<400> SEQUENCE: 33
gcaaggccct ggagctcttc                                        20

<210> SEQ ID NO 34
<211> LENGTH: 20
<212> TYPE: DNA
<213> ORGANISM: Artificial Sequence
<220> FEATURE:
<223> OTHER INFORMATION: Myoglobin R-primer

<400> SEQUENCE: 34
gcttggtggg ctggacagtg                                        20

<210> SEQ ID NO 35
<211> LENGTH: 20
<212> TYPE: DNA
<213> ORGANISM: Artificial Sequence
<220> FEATURE:
<223> OTHER INFORMATION: Tnnt1 F-primer

<400> SEQUENCE: 35
cccccgaaga ttccagaagg                                        20

<210> SEQ ID NO 36
<211> LENGTH: 22
<212> TYPE: DNA
<213> ORGANISM: Artificial Sequence
<220> FEATURE:
<223> OTHER INFORMATION: Tnnt1 R-primer

<400> SEQUENCE: 36
tgcggtcttt tagtgcaatg ag                                     22

<210> SEQ ID NO 37
<211> LENGTH: 21
<212> TYPE: DNA
<213> ORGANISM: Artificial Sequence

```
<220> FEATURE:
<223> OTHER INFORMATION: Tnni1 F-primer

<400> SEQUENCE: 37
atgccggaag ttgagaggaa a                                              21

<210> SEQ ID NO 38
<211> LENGTH: 20
<212> TYPE: DNA
<213> ORGANISM: Artificial Sequence
<220> FEATURE:
<223> OTHER INFORMATION: Tnni1 R-primer

<400> SEQUENCE: 38
tccgagaggt aacgcacctt                                                20

<210> SEQ ID NO 39
<211> LENGTH: 21
<212> TYPE: DNA
<213> ORGANISM: Artificial Sequence
<220> FEATURE:
<223> OTHER INFORMATION: Tnnc1 F-primer

<400> SEQUENCE: 39
gcggtagaac agttgacaga g                                              21

<210> SEQ ID NO 40
<211> LENGTH: 19
<212> TYPE: DNA
<213> ORGANISM: Artificial Sequence
<220> FEATURE:
<223> OTHER INFORMATION: Tnnc1 R-primer

<400> SEQUENCE: 40
ccagctcctt ggtgctgat                                                 19

<210> SEQ ID NO 41
<211> LENGTH: 21
<212> TYPE: DNA
<213> ORGANISM: Artificial Sequence
<220> FEATURE:
<223> OTHER INFORMATION: Aldoa F-primer

<400> SEQUENCE: 41
actctctgct gaccgggctc t                                              21

<210> SEQ ID NO 42
<211> LENGTH: 20
<212> TYPE: DNA
<213> ORGANISM: Artificial Sequence
<220> FEATURE:
<223> OTHER INFORMATION: Aldoa R-primer

<400> SEQUENCE: 42
aatgcttccg gtggactcat                                                20

<210> SEQ ID NO 43
<211> LENGTH: 21
<212> TYPE: DNA
<213> ORGANISM: Artificial Sequence
<220> FEATURE:
<223> OTHER INFORMATION: Pvalb F-primer

<400> SEQUENCE: 43
atcaagaagg cgataggagc c                                              21
```

```
<210> SEQ ID NO 44
<211> LENGTH: 19
<212> TYPE: DNA
<213> ORGANISM: Artificial Sequence
<220> FEATURE:
<223> OTHER INFORMATION: Pvalb R-primer

<400> SEQUENCE: 44
ggccagaagc gtctttgtt                                              19

<210> SEQ ID NO 45
<211> LENGTH: 20
<212> TYPE: DNA
<213> ORGANISM: Artificial Sequence
<220> FEATURE:
<223> OTHER INFORMATION: Tnnt3 F-primer

<400> SEQUENCE: 45
ggaacgccag aacagattgg                                             20

<210> SEQ ID NO 46
<211> LENGTH: 22
<212> TYPE: DNA
<213> ORGANISM: Artificial Sequence
<220> FEATURE:
<223> OTHER INFORMATION: Tnnt3 R-primer

<400> SEQUENCE: 46
tggaggacag agccttttc tt                                           22

<210> SEQ ID NO 47
<211> LENGTH: 22
<212> TYPE: DNA
<213> ORGANISM: Artificial Sequence
<220> FEATURE:
<223> OTHER INFORMATION: Tnni2 F-primer

<400> SEQUENCE: 47
agagtgtgat gctccagata gc                                          22

<210> SEQ ID NO 48
<211> LENGTH: 19
<212> TYPE: DNA
<213> ORGANISM: Artificial Sequence
<220> FEATURE:
<223> OTHER INFORMATION: Tnni2 R-primer

<400> SEQUENCE: 48
agcaacgtcg atcttcgca                                              19

<210> SEQ ID NO 49
<211> LENGTH: 21
<212> TYPE: DNA
<213> ORGANISM: Artificial Sequence
<220> FEATURE:
<223> OTHER INFORMATION: Tnnc2 F-primer

<400> SEQUENCE: 49
atggcagcgg tactatcgac t                                           21

<210> SEQ ID NO 50
<211> LENGTH: 22
<212> TYPE: DNA
<213> ORGANISM: Artificial Sequence
<220> FEATURE:
<223> OTHER INFORMATION: Tnnc2 R-primer
```

<400> SEQUENCE: 50
ccttcgcatc ctctttcatc tg                                          22

<210> SEQ ID NO 51
<211> LENGTH: 21
<212> TYPE: DNA
<213> ORGANISM: Artificial Sequence
<220> FEATURE:
<223> OTHER INFORMATION: GAPDH F-primer

<400> SEQUENCE: 51
gaagggcatc ttgggctaca c                                           21

<210> SEQ ID NO 52
<211> LENGTH: 24
<212> TYPE: DNA
<213> ORGANISM: Artificial Sequence
<220> FEATURE:
<223> OTHER INFORMATION: GAPDH R-primer

<400> SEQUENCE: 52
gcagcgaact ttattgatgg tatt                                        24

<210> SEQ ID NO 53
<211> LENGTH: 19
<212> TYPE: DNA
<213> ORGANISM: Artificial Sequence
<220> FEATURE:
<223> OTHER INFORMATION: CD36 F-primer

<400> SEQUENCE: 53
aatggcacag acgcagcct                                              19

<210> SEQ ID NO 54
<211> LENGTH: 18
<212> TYPE: DNA
<213> ORGANISM: Artificial Sequence
<220> FEATURE:
<223> OTHER INFORMATION: CD36 R-primer

<400> SEQUENCE: 54
ggttgtctgg attctgga                                               18

<210> SEQ ID NO 55
<211> LENGTH: 20
<212> TYPE: DNA
<213> ORGANISM: Artificial Sequence
<220> FEATURE:
<223> OTHER INFORMATION: LPL F-primer

<400> SEQUENCE: 55
gtacctgaag actcgctctc                                             20

<210> SEQ ID NO 56
<211> LENGTH: 20
<212> TYPE: DNA
<213> ORGANISM: Artificial Sequence
<220> FEATURE:
<223> OTHER INFORMATION: LPL R-primer

<400> SEQUENCE: 56
agggtgaagg gaatgttctc                                             20

<210> SEQ ID NO 57

```
<211> LENGTH: 20
<212> TYPE: DNA
<213> ORGANISM: Artificial Sequence
<220> FEATURE:
<223> OTHER INFORMATION: Fabp4 F-primer

<400> SEQUENCE: 57
gatgcctttg tgggaacctg                                                 20

<210> SEQ ID NO 58
<211> LENGTH: 20
<212> TYPE: DNA
<213> ORGANISM: Artificial Sequence
<220> FEATURE:
<223> OTHER INFORMATION: Fabp4 R-primer

<400> SEQUENCE: 58
tcctgtcgtc tgcggtgatt                                                 20

<210> SEQ ID NO 59
<211> LENGTH: 20
<212> TYPE: DNA
<213> ORGANISM: Artificial Sequence
<220> FEATURE:
<223> OTHER INFORMATION: Fto F-primer

<400> SEQUENCE: 59
gtcagagaga aggccaatga                                                 20

<210> SEQ ID NO 60
<211> LENGTH: 20
<212> TYPE: DNA
<213> ORGANISM: Artificial Sequence
<220> FEATURE:
<223> OTHER INFORMATION: Fto R-primer

<400> SEQUENCE: 60
tagcagtctc cctggtgaag                                                 20

<210> SEQ ID NO 61
<211> LENGTH: 19
<212> TYPE: DNA
<213> ORGANISM: Artificial Sequence
<220> FEATURE:
<223> OTHER INFORMATION: Pgc1 alpha F-primer

<400> SEQUENCE: 61
ccctgccatt gttaagacc                                                  19

<210> SEQ ID NO 62
<211> LENGTH: 19
<212> TYPE: DNA
<213> ORGANISM: Artificial Sequence
<220> FEATURE:
<223> OTHER INFORMATION: Pgc1 alpha R-primer

<400> SEQUENCE: 62
tgctgctgtt cctgttttc                                                  19

<210> SEQ ID NO 63
<211> LENGTH: 21
<212> TYPE: DNA
<213> ORGANISM: Artificial Sequence
<220> FEATURE:
<223> OTHER INFORMATION: Adiponectin F-primer

<400> SEQUENCE: 63
```

```
aatggcacac caggccgtga t                                      21

<210> SEQ ID NO 64
<211> LENGTH: 21
<212> TYPE: DNA
<213> ORGANISM: Artificial Sequence
<220> FEATURE:
<223> OTHER INFORMATION: Adiponectin R-primer

<400> SEQUENCE: 64
tctccaggct ctcctttcct g                                      21

<210> SEQ ID NO 65
<211> LENGTH: 23
<212> TYPE: DNA
<213> ORGANISM: Artificial Sequence
<220> FEATURE:
<223> OTHER INFORMATION: MYH3 variation F-primer

<400> SEQUENCE: 65
tggtctttcc taattggtga cat                                    23

<210> SEQ ID NO 66
<211> LENGTH: 22
<212> TYPE: DNA
<213> ORGANISM: Artificial Sequence
<220> FEATURE:
<223> OTHER INFORMATION: MYH3 variation R-primer

<400> SEQUENCE: 66
agttttgagc aaggcttttg tt                                     22

<210> SEQ ID NO 67
<211> LENGTH: 30
<212> TYPE: DNA
<213> ORGANISM: Sus scrofa

<400> SEQUENCE: 67
aatacagcag gaggactgct gttgttcccc                             30

<210> SEQ ID NO 68
<211> LENGTH: 24
<212> TYPE: DNA
<213> ORGANISM: Sus scrofa

<400> SEQUENCE: 68
gagacagcag gacgtgtgtt cccc                                   24
```